United States Patent
Chuang et al.

(10) Patent No.: US 11,320,427 B2
(45) Date of Patent: May 3, 2022

(54) TANDEMLY REPEATED ANTIBODY-BINDING PROTEIN AND ITS APPLICATIONS

(71) Applicant: TAIPEI MEDICAL UNIVERSITY, Taipei (TW)

(72) Inventors: Kuo-Hsiang Chuang, Taipei (TW); Yi-Jou Chen, Taipei (TW); Michael Chen, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 186 days.

(21) Appl. No.: 15/649,184

(22) Filed: Jul. 13, 2017

(65) Prior Publication Data

US 2019/0018005 A1     Jan. 17, 2019

(51) Int. Cl.
| | |
|---|---|
| *G01N 33/543* | (2006.01) |
| *C07K 14/315* | (2006.01) |
| *C07K 16/24* | (2006.01) |
| *C07K 14/195* | (2006.01) |
| *C07K 16/44* | (2006.01) |
| *C07K 16/28* | (2006.01) |
| *C07K 16/42* | (2006.01) |
| *C07K 16/00* | (2006.01) |

(52) U.S. Cl.
CPC ..... *G01N 33/54353* (2013.01); *C07K 14/195* (2013.01); *C07K 14/315* (2013.01); *C07K 16/00* (2013.01); *C07K 16/249* (2013.01); *C07K 16/2818* (2013.01); *C07K 16/4283* (2013.01); *C07K 16/44* (2013.01); *G01N 33/54306* (2013.01); *C07K 2319/03* (2013.01); *C07K 2319/42* (2013.01); *C07K 2319/70* (2013.01); *G01N 2333/315* (2013.01)

(58) Field of Classification Search
CPC .... C07K 14/315; C07K 14/195; C07K 16/00; C07K 16/249; C07K 16/2818; C07K 16/4283; C07K 16/44; C07K 2319/03; C07K 2319/42; C07K 2319/70; G01N 2333/315; G01N 33/54306; G01N 33/54353
See application file for complete search history.

(56) References Cited

U.S. PATENT DOCUMENTS

| | | | | |
|---|---|---|---|---|
| 2002/0082411 A1* | 6/2002 | Carter | ................ | A61K 39/0008 536/23.5 |
| 2010/0098719 A1* | 4/2010 | Van Endert | ........ | C07K 16/1275 424/193.1 |
| 2013/0323717 A1* | 12/2013 | Choe | ...................... | C07K 16/00 435/5 |
| 2014/0221613 A1* | 8/2014 | Honda | ................ | C07K 14/315 530/350 |
| 2016/0280744 A1* | 9/2016 | Honda | .................... | C07K 14/31 |
| 2017/0305965 A1* | 10/2017 | Yoshida | ................... | C07K 1/22 |

FOREIGN PATENT DOCUMENTS

| | | | | |
|---|---|---|---|---|
| CN | 106146627 A | * | 11/2016 | ............. C07K 16/00 |
| JP | 2011-050272 | * | 3/2011 | ............. C12N 15/09 |
| KR | 20130074621 A | * | 4/2013 | ............. G01N 33/53 |
| WO | WO-2009095033 A1 | * | 8/2009 | ............. A61K 39/39 |
| WO | WO-2016031926 A1 | * | 3/2016 | ............... C07K 1/22 |
| WO | WO-2016061427 A1 | * | 4/2016 | ....... G01N 33/54353 |

OTHER PUBLICATIONS

Olsson et al. "Structure and evolution of the repetitive gene encoding streptococcal protein G", Eur. J. Biochem. 168, 319-324 (1987).*
Translation for CN106146627 retrieved by Espacenet Patent Translate on Aug. 7, 2019 (26 pages total).*
Translation for CN106146627 retrieved by Google Patents on Aug. 7, 2019 (9 pages total).*
Translation for KR20130074621 retrieved by Espacenet Patent Translate on Aug. 8, 2019 (18 pages total).*
Espacenet translation for Matsuzaki et al., JP2011050272A (2011), 18 pages total.*
Google patents translation for Matsuzaki et al., JP2011050272A (2011), 7 pages total, retrieved from https://patents.google.com/patent/WO2016061427A1/en?oq=wo2016061427.*
UniProtKB Entry P19909—Comparing version 131 to 153, retrieved from https://www.uniprot.org/uniprot/P19909?version=131&version=153&diff=true on May 10, 2021, 6 pages total (Year: 2021).*
Hao et al., "Poly-protein G-expressing bacteria enhance the sensitivity of immunoassays"; Scientific Reports, vol. 7, Article No. 989 (2017); published online: Apr. 20, 2017 (the full text), pp. 1-11, DOI:10.1038/s41598-017-01022-w.
Lee et al., "Enhancing immunoassay detection of antigens with multimeric protein Gs"; Biosensors and Bioelectronics, 28 (2011), 146-151; Jul. 18, 2011 (the full text).
Konieczny et al., "Cell surface presentation of recombinant (poly-) peptides including functional T-cell epitopes by the AIDA autotransporter system" FEMS Immunology and Medical Microbiology, 27 (2000), 321-332 (the full text).
English Translation of Search Report for related Taiwan application No. 106123547, Date of completion of search: Jun. 8, 2018 (one page total).

* cited by examiner

*Primary Examiner* — Galina M. Yakovleva

(74) *Attorney, Agent, or Firm* — WPAT, P.C., Intellectual Property Attorneys; Anthony King

(57) ABSTRACT

The invention provides a tandemly repeated protein comprising at least two repeats of an amino acid sequence of an antibody binding protein or a fragment thereof and a cell having the repeats expressed on the membrane thereof, which can be used in immunoassay to improve detection sensitivity and detection limit.

11 Claims, 29 Drawing Sheets
Specification includes a Sequence Listing.

SEQUENCE LISTING

```
<160> NUMBER OF SEQ ID NOS: 4

<210> SEQ ID NO 1
<211> LENGTH: 55
<212> TYPE: PRT
<213> ORGANISM: Streptococcal bacteria

<400> SEQUENCE: 1

Thr Tyr Lys Leu Val Ile Asn Gly Lys Thr Leu Lys Gly Glu Thr Thr
1               5                   10                  15

Thr Glu Ala Val Asp Ala Ala Thr Ala Glu Lys Val Phe Lys Gln Tyr
```

```
            20                  25                  30
Ala Asn Asp Asn Gly Val Asp Gly Glu Trp Thr Tyr Asp Asp Ala Thr
            35                  40                  45

Lys Thr Phe Thr Val Thr Glu
         50                  55

<210> SEQ ID NO 2
<211> LENGTH: 5
<212> TYPE: PRT
<213> ORGANISM: artificial sequence
<220> FEATURE:
<223> OTHER INFORMATION: synthetic peptide

<400> SEQUENCE: 2

Gly Gly Gly Ser Gly
1               5

<210> SEQ ID NO 3
<211> LENGTH: 11
<212> TYPE: PRT
<213> ORGANISM: artificial sequence
<220> FEATURE:
<223> OTHER INFORMATION: synthetic peptide

<400> SEQUENCE: 3

Gly Gly Gly Gly Ser Gly Gly Gly Ser Val
1               5                   10

<210> SEQ ID NO 4
<211> LENGTH: 535
<212> TYPE: PRT
<213> ORGANISM: artificial sequence
<220> FEATURE:
<223> OTHER INFORMATION: synthetic polypeptide

<400> SEQUENCE: 4

Thr Tyr Lys Leu Val Ile Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
            35                  40                  45

Lys Thr Phe Thr Val Thr Glu Gly Gly Gly Ser Gly Gly Gly Gly
         50                  55                  60

Ser Val Glu Thr Tyr Lys Leu Val Ile Asn Gly Lys Thr Leu Lys Gly
65              70                  75                  80

Glu Thr Thr Thr Glu Ala Val Asp Ala Ala Thr Ala Glu Lys Val Phe
            85                  90                  95

Lys Gln Tyr Ala Asn Asp Asn Gly Val Asp Gly Glu Trp Thr Tyr Asp
            100                 105                 110

Asp Ala Thr Lys Thr Phe Thr Val Thr Glu Gly Gly Gly Ser Gly
            115                 120                 125

Gly Gly Ser Val Glu Thr Tyr Lys Leu Val Ile Asn Gly Lys Thr
        130                 135                 140

Leu Lys Gly Glu Thr Thr Thr Glu Ala Val Asp Ala Ala Thr Ala Glu
145                 150                 155                 160

Lys Val Phe Lys Gln Tyr Ala Asn Asp Asn Gly Val Asp Gly Glu Trp
            165                 170                 175

Thr Tyr Asp Asp Ala Thr Lys Thr Phe Thr Val Thr Glu Gly Gly Gly
            180                 185                 190
```

```
Gly Ser Gly Gly Gly Ser Val Glu Thr Tyr Lys Leu Val Ile Asn
            195                 200                 205
Gly Lys Thr Leu Lys Gly Glu Thr Thr Thr Glu Ala Val Asp Ala Ala
            210                 215                 220
Thr Ala Glu Lys Val Phe Lys Gln Tyr Ala Asn Asp Asn Gly Val Asp
225                 230                 235                 240
Gly Glu Trp Thr Tyr Asp Asp Ala Thr Lys Thr Phe Thr Val Thr Glu
                245                 250                 255
Gly Gly Gly Gly Ser Gly Gly Gly Ser Val Glu Thr Tyr Lys Leu
                260                 265                 270
Val Ile Asn Gly Lys Thr Leu Lys Gly Glu Thr Thr Thr Glu Ala Val
            275                 280                 285
Asp Ala Ala Thr Ala Glu Lys Val Phe Lys Gln Tyr Ala Asn Asp Asn
        290                 295                 300
Gly Val Asp Gly Glu Trp Thr Tyr Asp Asp Ala Thr Lys Thr Phe Thr
305                 310                 315                 320
Val Thr Glu Gly Gly Gly Gly Ser Gly Gly Gly Gly Ser Val Glu Thr
                325                 330                 335
Tyr Lys Leu Val Ile Asn Gly Lys Thr Leu Lys Gly Glu Thr Thr Thr
                340                 345                 350
Glu Ala Val Asp Ala Ala Thr Ala Glu Lys Val Phe Lys Gln Tyr Ala
                355                 360                 365
Asn Asp Asn Gly Val Asp Gly Glu Trp Thr Tyr Asp Asp Ala Thr Lys
            370                 375                 380
Thr Phe Thr Val Thr Glu Gly Gly Gly Gly Ser Gly Gly Gly Gly Ser
385                 390                 395                 400
Val Glu Thr Tyr Lys Leu Val Ile Asn Gly Lys Thr Leu Lys Gly Glu
                405                 410                 415
Thr Thr Thr Glu Ala Val Asp Ala Ala Thr Ala Glu Lys Val Phe Lys
            420                 425                 430
Gln Tyr Ala Asn Asp Asn Gly Val Asp Gly Glu Trp Thr Tyr Asp Asp
        435                 440                 445
Ala Thr Lys Thr Phe Thr Val Thr Glu Gly Gly Gly Gly Ser Gly Gly
        450                 455                 460
Gly Gly Ser Val Glu Thr Tyr Lys Leu Val Ile Asn Gly Lys Thr Leu
465                 470                 475                 480
Lys Gly Glu Thr Thr Thr Glu Ala Val Asp Ala Ala Thr Ala Glu Lys
                485                 490                 495
Val Phe Lys Gln Tyr Ala Asn Asp Asn Gly Val Asp Gly Glu Trp Thr
                500                 505                 510
Tyr Asp Asp Ala Thr Lys Thr Phe Thr Val Thr Glu Gly Gly Gly Gly
            515                 520                 525
Ser Gly Gly Gly Gly Ser Val
            530                 535
```

TANDEMLY REPEATED ANTIBODY-BINDING PROTEIN AND ITS APPLICATIONS

FIELD OF THE INVENTION

The present invention relates to the field of immunoassay. Particularly, the present invention relates to a tandemly repeated protein and its application in the detection of a target analyte.

BACKGROUND OF THE INVENTION

Immunoassays are used to quantify molecules of biological interest based on the specificity and selectivity of antibody reagents generated. Immunoassays are a group of sensitive analytical tests that utilize specific antibody/antigen complexes to produce a signal that can be measured and related to the concentration of a target analyte in solution, including enzyme-linked immunosorbent assay (ELISA), Western blot, flow cytometry and immunohistochemistry (IHC) etc. An antibody-based immunoassay utilizes an immunoreactant (antigen or antibody) bound on an immunosorbent (antigen or antibody bound to a solid support) through hydropbobic, hydrophilic or electric linkage. However, the following problems existed in the antibody-based immunoassay: (i) the loading amounts of the capture antibodies on the surface of the solid support are limited; (ii) the direction of the capture antibodies bound on the surface of the solid support are various, which result in sensitivity decrease because the antigen-binding region is located at the bottom of the solid support; (iii) a purified antibody must be used because other proteins may compete for the binding sites on the surface of the solid support with the capture antibodies, which causes a reduction of loading amount of the capture antibodies on the surface of the solid support. US 20110312104 provides a method for releasing, from a surface of a base plate, immunoglobulin G bound to the surface with use of protein A to measure analytes that are not only antigens with a high molecular weight but also antigens with a low molecular weight. However, this reference sill cannot totally avoid the above-mentioned problems.

Hence, there is still a need to improve immunoassay methods to have better sensitivity and specificity.

SUMMARY OF THE INVENTION

The invention provides a tandemly repeated protein, comprising at least two repeats of an amino acid sequence of an antibody IgG binding protein or a fragment thereof, and one or more linkers that link the repeats to each other. In some embodiments, the antibody IgG binding protein is protein A, protein G, protein A/G, protein L or Fc receptor, or a fragment, a combination or a fragment combination thereof.

In some embodiments, the tandemly repeated protein comprises 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 2 to 16, 3 to 16, 4 to 16, 5 to 16, 6 to 16, 7 to 16, 8 to 16, 9 to 16, 10 to 16, 11 to 16, 12 to 16, 2 to 14, 3 to 14, 5 to 14, 6 to 14, 7 to 14, 8 to 14, 9 to 14, 10 to 14, 2 to 12, 3 to 12, 4 to 12, 5 to 12, 6 to 12, 7 to 12, 8 to 12, 9 to 12, 2 to 10, 3 to 10, 4 to 10, 5 to 10, 6 to 10, 7 to 10, 2 to 9, 3 to 9, 4 to 9, 5 to 9 or 6 to 9 repeats of an amino acid sequence of an antibody IgG binding protein or a fragment thereof. In a further embodiment, the tandemly repeated protein comprises 8 repeats of an amino acid sequence of an antibody IgG binding protein or a fragment thereof. The exemplary embodiments of the amino acid sequences include, but are not limited to, the sequence of C1, C2 or C3 fragment of protein G. The preferred embodiment of the amino acid sequence of the C2 fragment of the protein G is SEQ ID NO:1.

The linkers used in the tandemly repeated protein may be the same or different. Exemplary embodiments of the linker includes, but are not limited to, an amino acid sequence of GGGSG (SEQ ID NO:2) or GGGGSGGGGSV (SEQ ID NO:3).

Exemplary embodiments of the tandemly repeated protein also include, but are not limited to, 8 repeats of an amino acid sequence of a protein G or a fragment thereof and a linker comprising an amino acid sequence of SEQ ID NO:2 or SEQ ID NO:3; 8 repeats of an amino acid sequence of SEQ ID NO:1 and linkers comprising an amino acid sequence of SEQ ID NO:2 or SEQ ID NO:3 to link the repeats to each other; and the tandemly repeated protein comprises the amino acid sequence of SEQ ID NO:4.

The invention provides a cell comprising a tandemly repeated protein expressed on the membrane of the cell, wherein the tandemly repeated protein is fused with the transmembrane protein of the cell.

The invention also provides an antibody-repeated protein complex, comprising multiple antibodies or fragments thereof binding to a tandemly repeated protein of the invention or binding to a cell of the invention. In one embodiment, the antibody is a detection antibody or a capture antibody.

The invention also provides a method for detection of an analyte in a sample, comprising using a tandemly repeated protein, cell and antibody-repeated protein complex of the invention to capture the analyte in a sample in an immunoassay or an antibody-coated immunoassay, and qualitatively or quantitatively detecting the analyte.

In one embodiment for western blot and ELISA, the method for detecting an analyte in a sample comprises the steps of:

providing a solid support optionally coating with an analyte;
binding multiple detection antibodies to a tandemly repeated protein of the invention, or a cell of the invention to form a detection antibody complex;
binding the detection antibody complex to the analyte coated in the solid support; and
qualitatively or quantitatively detecting the analyte.

In one embodiment for sandwich ELISA, the method for detection of an analyte in a sample comprises the steps of:
providing a solid support;
immobilizing a capture antibody on the solid support;
capturing the analyte in a sample by the capture antibody;
binding multiple detection antibodies to the tandemly repeated protein of the invention, or the cell of the invention to form a detection antibody complex;
adding the detection antibody complex to bind to the analyte; and
qualitatively or quantitatively detecting the analyte.

In one embodiment for sandwich ELISA, the method for detection of an analyte in a sample comprises the steps of:
providing a solid support;
immobilizing a tandemly repeated protein of the invention, or a cell of the invention on the solid support;
binding multiple capture antibodies to the tandemly repeated protein of the invention, or the cell of the invention;
capturing the analyte in a sample by the capture antibody complex;
adding a detection antibody to bind to the analyte; and
qualitatively or quantitatively detecting the analyte.

In one embodiment for competition ELISA, the method for detection of an analyte in a sample comprises the steps of:
providing a solid support;
immobilizing a tandemly repeated protein of the invention, or a cell of the invention on the solid support;
binding multiple capture antibodies to the tandemly repeated protein of the invention, or the cell of the invention to form a capture antibody complex;
mixing a signal labeled analyte having a predetermined concentration with the analyte in a sample to form a mixture;
capturing the analyte of the mixture by the capture antibody complex; and
qualitatively or quantitatively detecting the analyte.

The invention also provides a kit for detecting an analyte in a sample, comprising a solid support optionally coated with an antigen, the analyte or a capture antibody; and a tandemly repeated protein of the invention, or a cell of the invention. In one embodiment, the kit further comprises a detection antibody or a capture antibody. In one embodiment, the detection antibody can be further labeled.

The invention further provides a kit for detecting an analyte in a sample using western blot or ELISA, comprising a solid support optionally coated with an analyte and a tandemly repeated protein of the invention, or a cell of the invention. In one embodiment, a kit for detecting an analyte in a sample using sandwich ELISA, comprising a solid support and a tandemly repeated protein of the invention, or the cell of the invention. In one embodiment, the invention provides a kit for detecting an analyte in a sample using competition ELISA, comprising a solid support coating with a tandemly repeated protein of the invention, or a cell of the invention and a tandemly repeated protein of the invention, or the cell of the invention.

In a further embodiment, the detection antibody described herein can be further labeled.

DETAILED DESCRIPTION OF THE INVENTION

Figure 1:
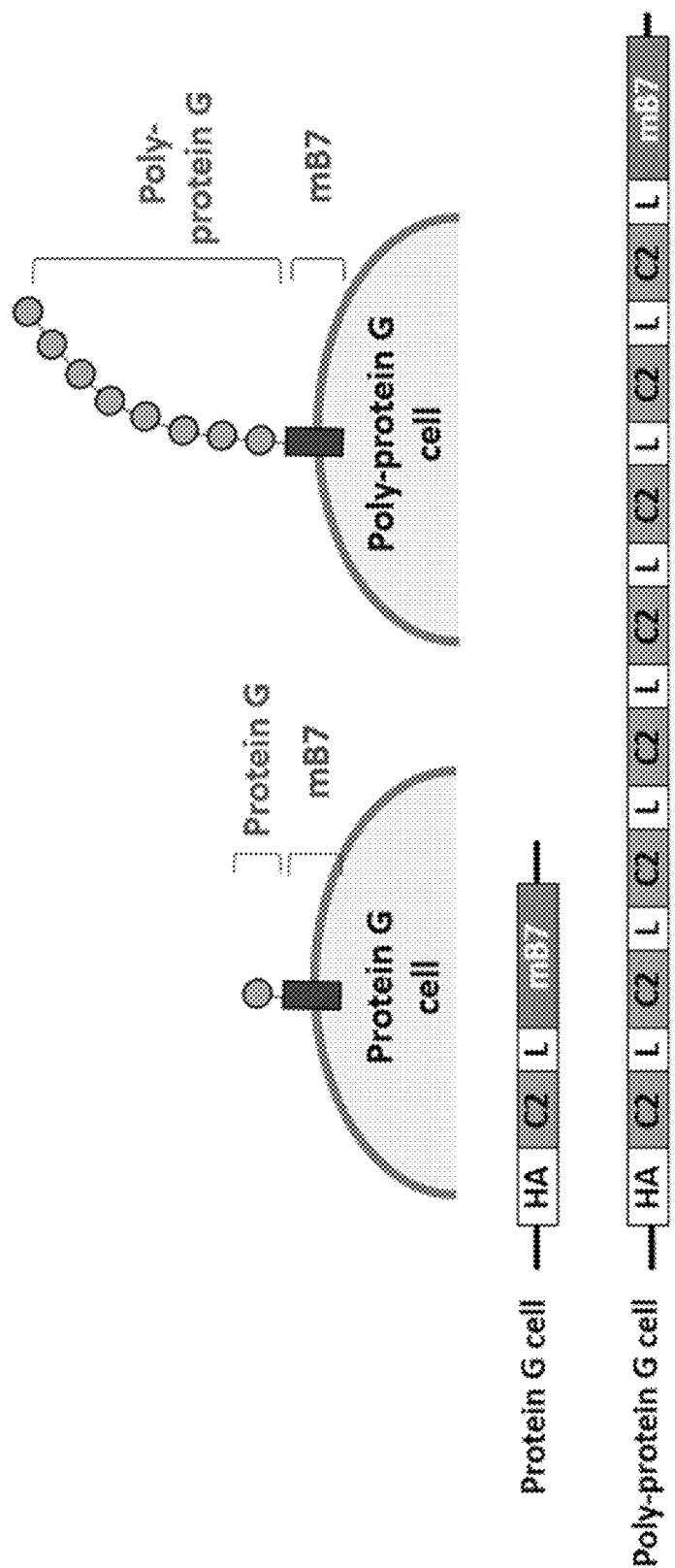
FIG. 1 shows the gene sequence of the poly-protein G of the invention, which is expressed on the membrane of the cell. For the protein G cell, the sequences include, from the N terminus to the C terminus, human influenza hemagglutinin (HA), protein G (C2), linker (L) and mB7. For the poly-protein G cell, the sequences include, from the N terminus to the C terminus, HA, C2, L, C2, L, C2, L, C2, L, C2, L, C2, L, C2, L, C2, L and mB7.

The invention provides a tandemly repeated protein comprising at least two repeats of an amino acid sequence of an antibody IgG binding protein or a fragment thereof and a cell having the repeats expressed on the membrane thereof, which can be used in an immunoassay to improve detection sensitivity and detection limit.

Terms used in the claims and specification are to be construed in accordance with their usual meaning as understood by one skilled in the art except as defined below.

It should be noted that, as used in this specification and the appended claims, the singular forms "a," "an" and "the" include plural referents unless the context clearly dictates otherwise.

As used herein, the use of "or" means "and/or" unless stated otherwise. In the context of a multiple dependent claim, the use of "or" refers back to more than one preceding independent or dependent claim in the alternative only.

As used herein, the term "analyte" or "target analyte" is used interchangeably, and generally refers to a substance, or set of substances in a sample that are detected and/or measured.

As used herein, the term "binding molecule," refers to a molecule that is capable of binding another molecule of interest.

As used herein, the term "analyte-binding" molecule refers to any molecule (such as an antibody) capable of participating in a specific binding reaction with an analyte molecule.

As used herein, the term "detecting" or "detection" is intended to include both quantitative and qualitative determination in the sense of obtaining an absolute value for the amount or concentration of the analyte present in the sample, and also obtaining an index, ratio, percentage, visual or other value indicative of the level of analyte in the sample. Assessment may be direct or indirect and the chemical or biochemical species actually detected need not of course be the analyte itself but may, for example, be a derivative thereof.

As used herein, the term "antibody" generally comprises monoclonal and polyclonal antibodies and binding fragments thereof, in particular Fc-fragments as well as so called "single-chain-antibodies," chimeric, humanized, in particular CDR-grafted antibodies, and dia or tetrabodies. Also comprised are immunoglobulin-like proteins that are selected through techniques including, for example, phage display to specifically bind to the molecule of interest contained in a sample. In this context the terms "specific" and "specific binding" refer to antibodies raised against the molecule of interest or a fragment thereof.

As used herein, the term "immobilized" refers to reagents being fixed to a solid surface. When a reagent is immobilized to a solid surface, it is either non-covalently bound or covalently bound to the surface.

In one aspect, the invention provides a tandemly repeated protein, comprising at least two repeats of an amino acid sequence of an antibody IgG binding protein or a fragment thereof, and one or more linkers that links the repeats to each other. In some embodiments, the antibody IgG binding protein is protein A, protein G, protein A/G, protein L or Fc receptor, or a fragment, a combination or a fragment combination thereof. The antibody IgG binding proteins are commerically available (for example, those sold by Thermo Fisher Scientific Inc.) and known in the art.

Protein A, Protein G, Protein A/G and Protein L are native and recombinant proteins of microbial origin that bind to mammalian immunoglobulin molecules. These proteins are available in purified, salt-free, lyophilized form, as well as coated in microplates and covalently immobilized to various solid supports.

Protein A is a 42 kDa surface protein originally found in the cell wall of the bacteria *Staphylococcus aureus*. It has found use in biochemical research because of its ability to bind immunoglobulins. It is composed of five homologous Ig-binding domains that fold into a three-helix bundle. Each domain is able to bind proteins from many mammalian species, most notably IgGs.

Protein A/G is a recombinant fusion protein that includes the IgG-binding domains of both Protein A and Protein G. Therefore, Protein A/G can be used for binding the broadest range of IgG subclasses from rabbit, mouse, human and other mammalian samples.

Protein L binds to certain immunoglobulin kappa light chains. Because kappa light chains occur in members of all classes of immunoglobulin (i.e., IgG, IgM, IgA, IgE and IgD), Protein L can purify these different classes of antibody. However, only those antibodies within each class that possess the appropriate kappa light chains will bind. Generally, empirical testing is required to determine if Protein L is effective for purifying a particular antibody.

Protein G is an immunoglobulin-binding protein expressed in group C and G *Streptococcal* bacteria and has found application in purifying antibodies through its binding to the Fab and Fc region. The C terminus of protein G can bind to an antibody. In the amino acid sequence of the protein G, the amino acids 306-331 are C1 fragment, the amino acids 347-402 is C2 fragment and the amino acids 418-473 are C3 fragment. Among the fragments, C1 and C3 can bind to Fc fragment and Fab fragment of an antibody and C2 can bind to Fc fragment of an antibody.

In some embodiments, the tandemly repeated protein comprises 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 2 to 16, 3 to 16, 4 to 16, 5 to 16, 6 to 16, 7 to 16, 8 to 16, 9 to 16, 10 to 16, 11 to 16, 12 to 16, 2 to 14, 3 to 14, 5 to 14, 6 to 14, 7 to 14, 8 to 14, 9 to 14, 10 to 14, 2 to 12, 3 to 12, 4 to 12, 5 to 12, 6 to 12, 7 to 12, 8 to 12, 9 to 12, 2 to 10, 3 to 10, 4 to 10, 5 to 10, 6 to 10, 7 to 10, 2 to 9, 3 to 9, 4 to 9, 5 to 9 or 6 to 9 repeats of an amino acid sequence of an antibody IgG binding protein or a fragment thereof. In a further embodiment, the tandemly repeated protein comprises 8 repeats of an amino acid sequence of an antibody IgG binding protein or a fragment thereof. In some embodiments, the antibody IgG binding protein or a fragment thereof is a protein A, protein G, protein A/G, protein L or Fc receptor or a fragment thereof. In some embodiments a protein A, protein G, protein A/G, protein L or Fc receptor or a fragment, a combination or a fragment combination thereof.

In some embodiments, the amino acid sequence of an antibody IgG binding protein or a fragment thereof comprises the sequence of C1, C2 or C3 fragment of protein G. In a further embodiment, the amino acid sequence comprises the sequence of C2 fragment of protein G.

In one embodiment, the amino acid sequence of the C2 fragment of the protein G is as follows.

```
                                               (SEQ ID NO: 1)
TYKLVINGKTLKGETTTEAVDAATAEKVFKQYANDNGVDGEWTYDDATKTF

TVTE
```

In some embodiments, the linkers used in the tandemly repeated protein may be the same or different. In some embodiments, the linker comprises an amino acid sequence of

```
                                               (SEQ ID NO: 2)
            GGGSG
            or (SEQ ID NO: 3)
            GGGGSGGGGSV.
```

In some embodiments, the tandemly repeated protein comprises 8 repeats of an amino acid sequence of a protein G or a fragment thereof and a linker comprising an amino acid sequence of SEQ ID NO:2 or SEQ ID NO:3. In one embodiment, the tandemly repeated protein comprises 8 repeats of an amino acid sequence of SEQ ID NO:1 and the linkers comprising an amino acid sequence of SEQ ID NO:2 or SEQ ID NO:3 to link the repeats to each other. In a further embodiment, the tandemly repeated protein comprises an amino acid sequence of SEQ ID NO:4.

```
                                               (SEQ ID NO: 4)
TYKLVINGKTLKGETTTEAVDAATAEKVFKQYANDNGVDGEWTYDDATKT

FTVTEGGGGSGGGGSVETYKLVINGKTLKGETTTEAVDAATAEKVFKQYA

NDNGVDGEWTYDDATKTFTVTEGGGGSGGGGSVETYKLVINGKTLKGETT

TEAVDAATAEKVFKQYANDNGVDGEWTYDDATKTFTVTEGGGGSGGGGSV

ETYKLVINGKTLKGETTTEAVDAATAEKVFKQYANDNGVDGEWTYDDATK

-continued
TFTVTEGGGGSGGGGSVETYKLVINGKTLKGETTTEAVDAATAEKVFKQY

ANDNGVDGEWTYDDATKTFTVTEGGGGSGGGGSVETYKLVINGKTLKGET

TTEAVDAATAEKVFKQYANDNGVDGEWTYDDATKTFTVTEGGGGSGGGGS

VETYKLVINGKTLKGETTTEAVDAATAEKVFKQYANDNGVDGEWTYDDAT

KTFTVTEGGGGSGGGGSVETYKLVINGKTLKGETTTEAVDAATAEKVFKQ

YANDNGVDGEWTYDDATKTFTVTEGGGGSGGGGSV
```

In another aspect, the invention provides a cell, comprising a tandemly repeated protein expressed on the membrane of the cell, wherein the tandemly repeated protein is fused with the transmembrane protein of the cell.

In another aspect, the invention provides an antibody-repeated protein complex, comprising multiple antibodies or fragments thereof binding to a tandemly repeated protein of the invention or binding to a cell of the invention. In one embodiment, the antibody is a detection antibody or a capture antibody.

The tandemly repeated protein, cell and antibody-repeated protein complex of the invention can be used in immunoassay; particularly, ELISA and antibody-coated immunoassay. The tandemly repeated protein, cell and antibody-repeated protein complex of the invention provide high antibody binding ability, increase the amounts of the detection antibody accumulated in the solid support, and can use unpurified detection antibody or capture antibody in the immunoassay. Accordingly, the invention provides kits and methods of using the tandemly repeated protein, cell and/or antibody-repeated protein complex of the invention in immunoassay.

In another aspect, the invention provides a method for detection of an analyte in a sample, comprising using a tandemly repeated protein, cell and/or antibody-repeated protein complex of the invention to capture the analyte in a sample in an immunoassay or an antibody-coated immunoassay, and qualitatively or quantitatively detecting the analyte.

In one embodiment, the method for detection of an analyte in a sample comprises the steps of:

providing a solid support optionally coating with an analyte;

binding multiple detection antibodies to a tandemly repeated protein of the invention, or a cell of the invention to form a detection antibody complex;

binding the detection antibody complex to the analyte coated in the solid support; and qualitatively or quantitatively detecting the analyte.

The above-mentioned embodiment is suitable for western blot and ELISA.

In one embodiment, the method for detection of an analyte in a sample comprises the steps of:

providing a solid support;

immobilizing a capture antibody on the solid support;

capturing the analyte in a sample by the capture antibody;

binding multiple detection antibodies to the tandemly repeated protein of the invention, or the cell of the invention to form a detection antibody complex;

adding the detection antibody complex to bind to the analyte; and qualitatively or quantitatively detecting the analyte.

The above-mentioned embodiment is suitable for sandwich ELISA.

In one embodiment, the method for detection of an analyte in a sample comprises the steps of:
providing a solid support;
immobilizing a tandemly repeated protein of the invention, or a cell of the invention on the solid support;
binding multiple capture antibodies to the tandemly repeated protein of the invention, or the cell of the invention;
capturing the analyte in a sample by the capture antibody complex;
adding a detection antibody to bind to the analyte; and
qualitatively or quantitatively detecting the analyte.

The above-mentioned embodiment is suitable for sandwich ELISA.

In one embodiment, the method for detection of an analyte in a sample comprises the steps of:
providing a solid support;
immobilizing a tandemly repeated protein of the invention, or a cell of the invention on the solid support;
binding multiple capture antibodies to the tandemly repeated protein of the invention, or the cell of the invention to form a capture antibody complex;
mixing a signal labeled analyte having a predetermined concentration with the analyte in a sample to form a mixture;
capturing the analyte in the mixture by the capture antibody complex; and
qualitatively or quantitatively detecting the analyte.

The above-mentioned embodiment is suitable for competition ELISA.

In another aspect, the invention provides a kit for detecting an analyte in a sample, comprising a solid support optionally coated with an antigen, the analyte or a capture antibody; and a tandemly repeated protein of the invention, or a cell of the invention. In one embodiment, the kit further comprises a detection antibody or a capture antibody. In one embodiment, the detection antibody can be further labeled. Whether or which one of the antigen, the analyte or the capture antibody optionally is coated on the solid support depends on the type of the immunoassay.

In one embodiment, the invention provides a kit for detecting an analyte in a sample using western blot or ELISA, comprising a solid support optionally coated with an analyte and a tandemly repeated protein of the invention, or a cell of the invention.

In one embodiment, the the invention provides a kit for detecting an analyte in a sample using sandwich ELISA, comprising a solid support and a tandemly repeated protein of the invention, or the cell of the invention.

In one embodiment, the invention provides a kit for detecting an analyte in a sample using competition ELISA, comprising a solid support coated with a tandemly repeated protein of the invention, or a cell of the invention and a tandemly repeated protein of the invention, or the cell of the invention.

The solid support used for immobilization of the tandemly repeated protein or the antibody-repeated protein complex may be any inert support or carrier that is essentially water insoluble and useful in immunoassays, including supports in the form of, e.g., flat surfaces, particles, porous matrices, etc. Examples of commonly used supports include small sheets, beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices may be used such as cyanogen bromide-activated carbohydrates and the reactive substrates. In one embodiment, the immobilized capture reagent is coated on a streptavidin-coated 96 well microtiter plate.

To facilitate the immunoassays, the detection antibody used in the kits and methods of the invention may also comprise a detectable label. The detectable label may be any moiety that does not interfere with the binding of the anlayte to the detection antibody and the binding to the tandemly repeated protein of the invention, or a cell of the invention.

Numerous labels are available to the methods and kit of the invention. Examples of the labels include, but are not limited to, radioisotopes, colloidal gold particles, fluorescent or chemilluminescent labels and enzymatic labels. Examples of the radioisotopes include, but are not limited to, $^{35}S$, $^{14}C$, $^{125}I$, $^{3}H$, and $^{131}I$. The antibody can be labeled with the radioisotope using techniques known in the art and radioactivity can be measured using scintillation counting. Other radionuclides include $^{99}Tc$, $^{90}Y$, $^{111}In$, $^{32}P$, $^{11}C$, $^{15}O$, $^{13}N$, $^{18}F$, $^{51}Cr$, $^{57}To$, $^{226}Ra$, $^{60}Co$, $^{59}Fe$, $^{57}Se$, $152Eu$, $^{67}CU$, $217Ci$ and $^{212}Pb$. Example of the fluorescent or chemilluminescent labels include, but are not limited to, rare earth chelates (europium chelates), fluorescein and derivatives, rhodamine and its derivatives, isothiocyanate, phycoerythrin, phycocyanin, allophycocyanin, o-phthaladehyde, fluorescamine, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, a ruthenylated amine reactive, N-hydroxysuccinimide ester label, Texas Red, dansyl, Lissamine, umbelliferone, phycocrytherin, phycocyanin, or commercially available fluorophores. The fluorescent labels can be conjugated to the antibody using techniques known in the art. Fluorescence can be quantified using a fluorimeter. Biotin label can be conjugated to the antibody using the techniques known in the art. Biotin-labeled antibody can be detected by enzyme-conjugated avidin and streptavidin. Examples of enzymatic labels include luciferases, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are known in the art.

When the detection antibody is labeled, the kits and methods may also comprise one or more reagents capable of producing a detectable signal when a sandwich is formed between the capture antibody, the analyte and the detector binding molecule. For enzyme-labeled detector binding molecules, the kit and methods may include substrates and cofactors required by the enzyme, and for fluorophore labels, the kit may include a dye precursor that produces a detectable chromophore. For biotin-labeled detector binding molecules, may include enzyme-conjugated avidin and streptavidin, substrates and cofactors required by the enzyme. If the detection antibody is not labeled, the kit and methods may also comprise a detection means and a step of using the detection means, respectively, such as a labeled antibody that specifically binds to the detection antibody.

The sample described herein may be any of a variety of body fluids, including tissue, biopsy, biosection, blood, serum, semen, breast exudate, saliva, sputum, urine, cytosols, plasma, ascites, pleural effusions, amniotic fluid, bladder washes, bronchioalveolar lavages, and cerebrospinal fluid. In some embodiments, the sample is tissue, biopsy, blood, serum or plasma, and in one preferred embodiment, the sample is serum.

The examples of the immunoassay include, but are not limited to, ELISA, western blot, flow cytometry, immunohistochemistry, radioimmunoassay, competitive immunoassay, magnetic immunoassay, memory lymphocyte immunostimulation assay (MELISA), lateral flow immunochromatographic assay, surround optical fiber immunoassay (SOFIA) and agglutination-PCR (ADAP).

In immunoassay such as ELISA and western blot, the tandemly repeated protein or the cell of the invention can bind multiple detection antibody to form a complex to increase the amounts of the detection antibody accumulated in the location of the analyte to be bound to the detection antibody. Accordingly, the detection efficiency is largely elevated and the detection sensitivity is increased as well.

In an antibody-based immunoassay such as sandwich ELISA or competition ELISA, the tandemly repeated protein or the cell of the invention can immobilize on the solid support to increase the load of the capture antibody on the solid support. Accordingly, the amounts of the analyte to be captured is increased and the detection sensitivity is also improved.

Particularly, the present invention relates to a recombinant protein, named tandemly repeated protein, which is constructed from the fragment (Fc)-binding domain of protein by gene engineering technologies. The tandemly repeated protein exhibits a much greater binding efficiency and affinity to antibody than monomer protein does. By coating the tandemly repeated protein on a solid phase plate (e.g. plate, membrane and bead), the antibody-loading amount on the plate can significantly increase and the display of antigen binding domain (Fab) of antibody on the plate can be unidirectional (outward). Another application of the tandemly repeated protein is to generate poly-protein/antibody complexes by mixing the tandemly repeated protein with antibodies, which increases the accumulated amount of the antibodies on the antigen area. Moreover, the invention relates to a cell expressing the tandemly repeated protein on the membrane thereof, which expresses the tandemly repeated protein on cell surface. By coating the cells on a solid phase plate, the antibody-loading amount on the plate can significantly increase and the display of antigen binding domain (Fab) of antibody on the plate can be unidirectional (outward). Another application of the cells is to generate the cell/antibody complexes by simply mixing the cells with antibodies, which increases the accumulated amount of the antibodies on the antigen area. Pairing with the tandemly repeated protein or the cells allows direct application of antibodies to immunoassays without additional purification. The invention can dramatically improve the sensitivities and detection limits of immunoassays using various antibodies.

The invention will be further understood with reference to the following non-limiting experimental examples.

EXAMPLE

Example 1 Cell Line Expressing the Tandemly Repeated Protein of the Invention (Poly Protein G) and its Antibody Capture Ability Construction of Poly Protein G The C2 domain of *Streptococcal* protein G was sequenced and cloned to produce one protein G-C2 domain and eight repeats of protein G-C2 domain (the amino acid sequence of one repeat is SEQ ID NO:1). The B7 transmembrane protein was linked to the C-terminus of the resulting domains to form protein G-mB7 and poly-protein G-mB7. The gene sequences from N- to C-terminus were HA-protein G-linker-mB7 and HA-poly-protein G-linker-mB7, respectively (see FIG. 1).

Cell Line Stably Expressing the Poly-Protein G

Figure 2:
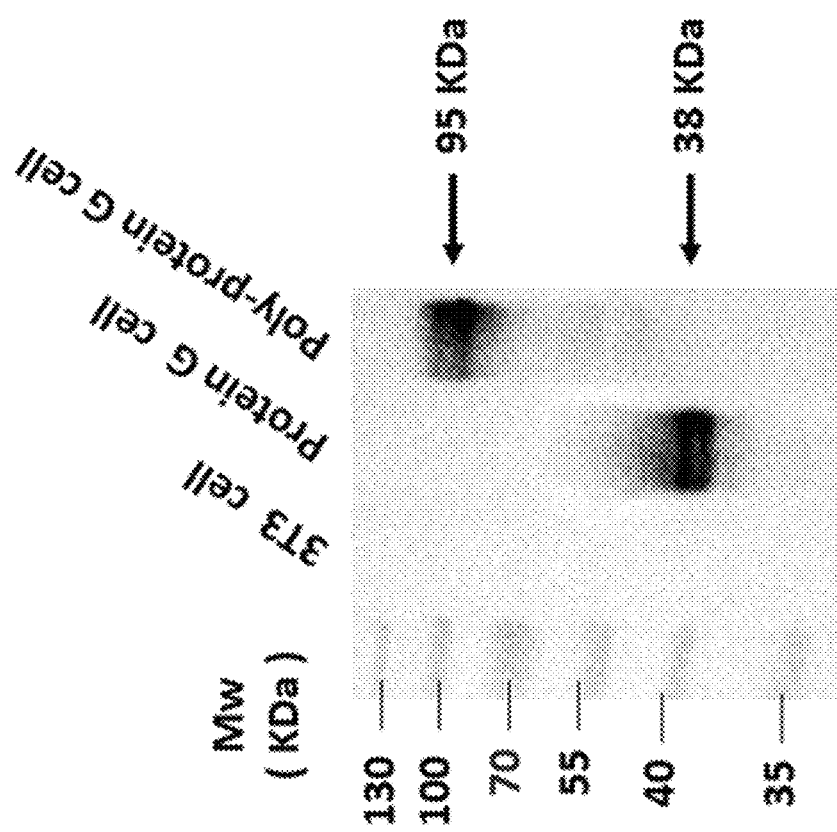
FIG. 2 shows the protein G expression in the protein G cell and the poly-protein G cell by Western blot. Lane 1: 3T3 cell; Lane 2: protein G cell; and Lane 3: poly-protein G cell.

The gene sequence was inserted into vector lentivirus and the resulting vectors were transfected into the 3T3 cell line to form Protein G cell and poly-protein G cell, respectively. The cell membrane proteins were collected and confirmed by western blot by adding mouse anti-HA antibody and HRP Goat anti-mouse IgG Fcγantibody to confirm whether the protein G and the poly-protein G are correctly expressed. As shown in FIG. 2, protein-G-mB7 (molecule weight: 38 KDa) and poly-protein-G-mB7 (95 KDa) are correctly expressed on the membrane of the cells.

Capture of Antibody by Poly-Protein G Cell

Figure 3:
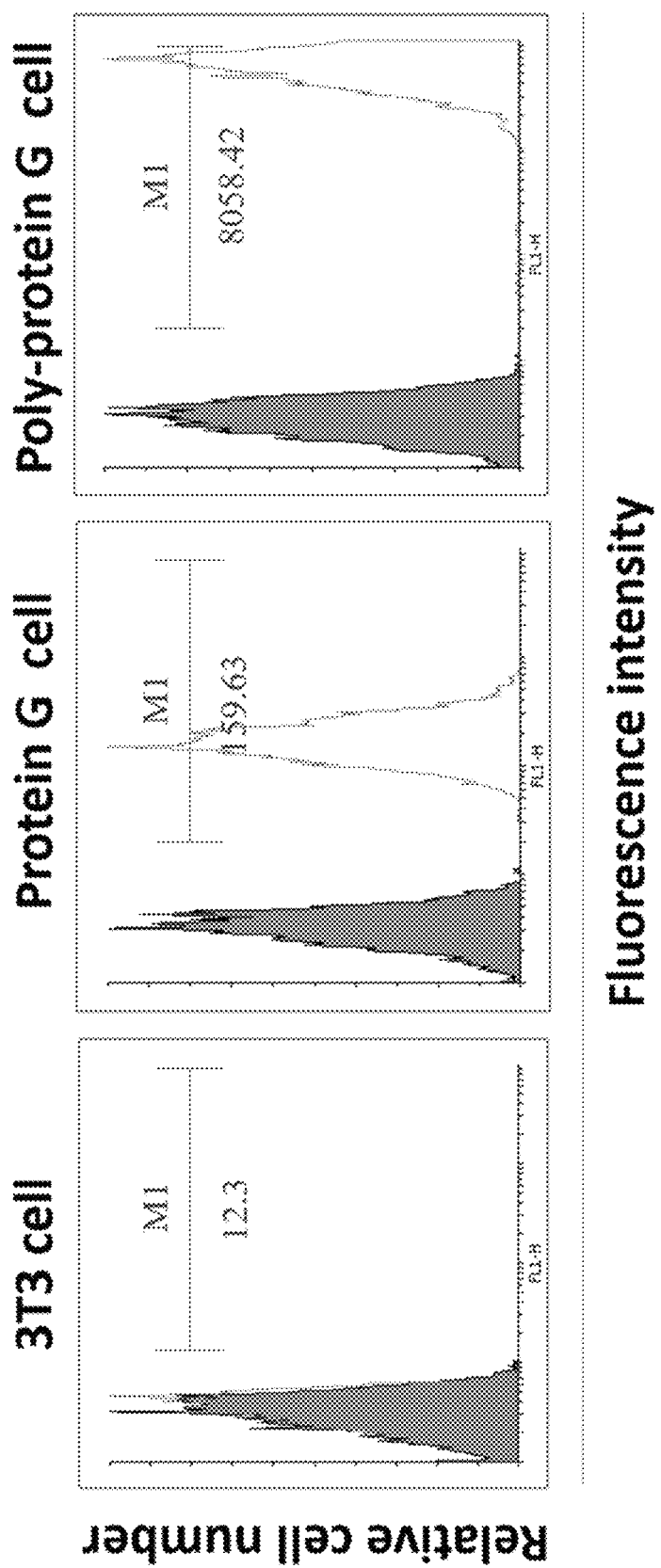
FIG. 3 shows the ability of the protein G cell and the poly-protein G cell in capturing the antibody. Left plot: 3T3 cell; middle plot: protein G cell; and right plot: poly-protein G cell.

FITC conjugated Goat anti-mouse immunoglobulin G Fcγantibody was added to the protein G cell or poly-protein G cell, respectively for a binding assay. The binding intensity was measured by flow cytometry. The results show that the fluorescence intensity of the protein G cell and poly-protein G cell are 159.63 and 8058.42 (see FIG. 3). It proves that the protein G cell or poly-protein G cell is stably expressed on the cell membrane and can bind to the antibody well. Unexpectedly, the ability of the poly-protein G cell to bind antibody is more than 50 times that of the protein G cell.

Specificity of the Antibody that Binds to the Poly-Protein G

Figure 4:
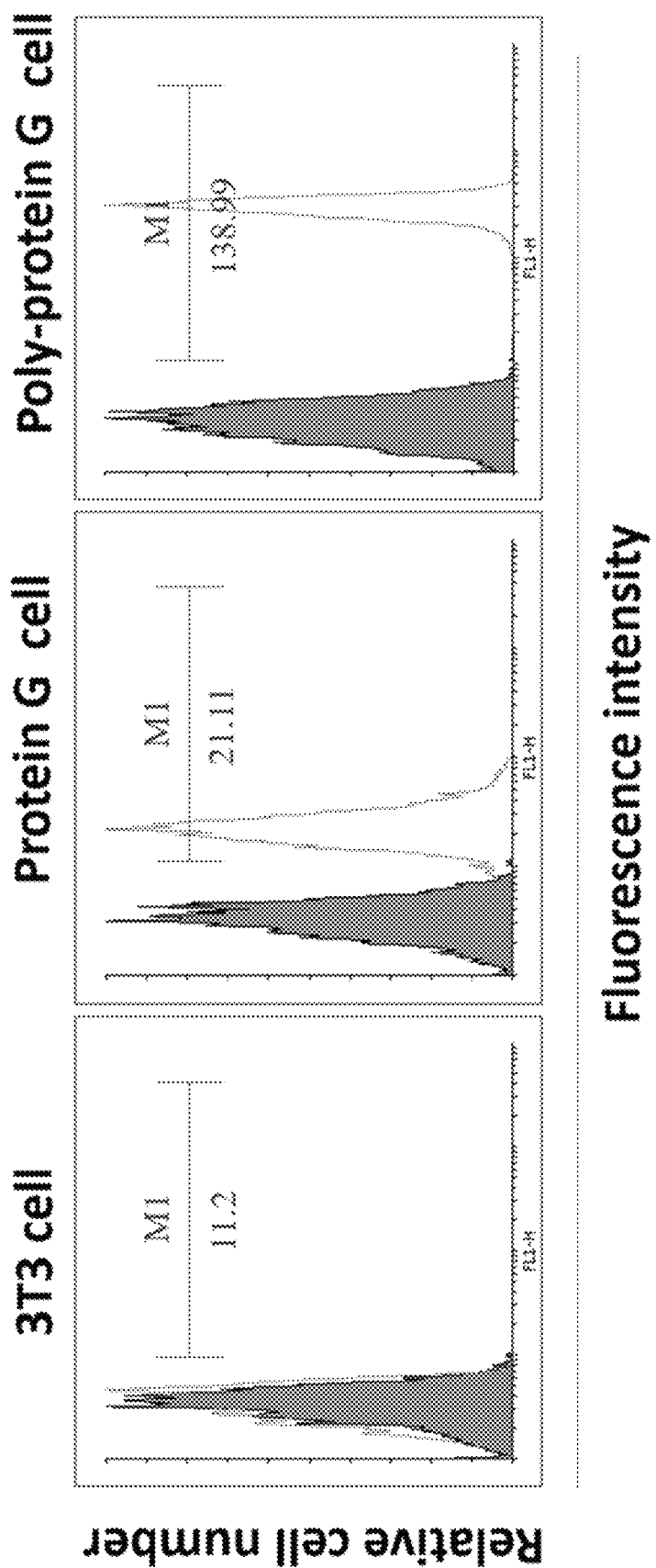
FIG. 4 shows the antigen binding ability of the antibody captured by the protein G cell and the poly-protein G cell. Left: 3T3 cell; middle plot: protein G cell; and right plot: poly-protein G cell.

The protein G cell and the poly-protein G cell were added to 3.3 antibody (an anti-PEG antibody) and then FITC conjugated 4-arm PEG was added. Flow cytometry was used to determine the fluorescence intensity on the cell surface. The fluorescence intensity of protein G cell and poly-protein G cell are 21.11 and 138.99, respectively (see FIG. 4). The results show that the 3.3 antibody binding to the protein G cell or poly-protein G cell still can bind to FITC conjugated 4-arm PEG and thus prove that the antibody maintains its specificity after it binds to the protein G cell or poly-protein G cell.

Figure 5:
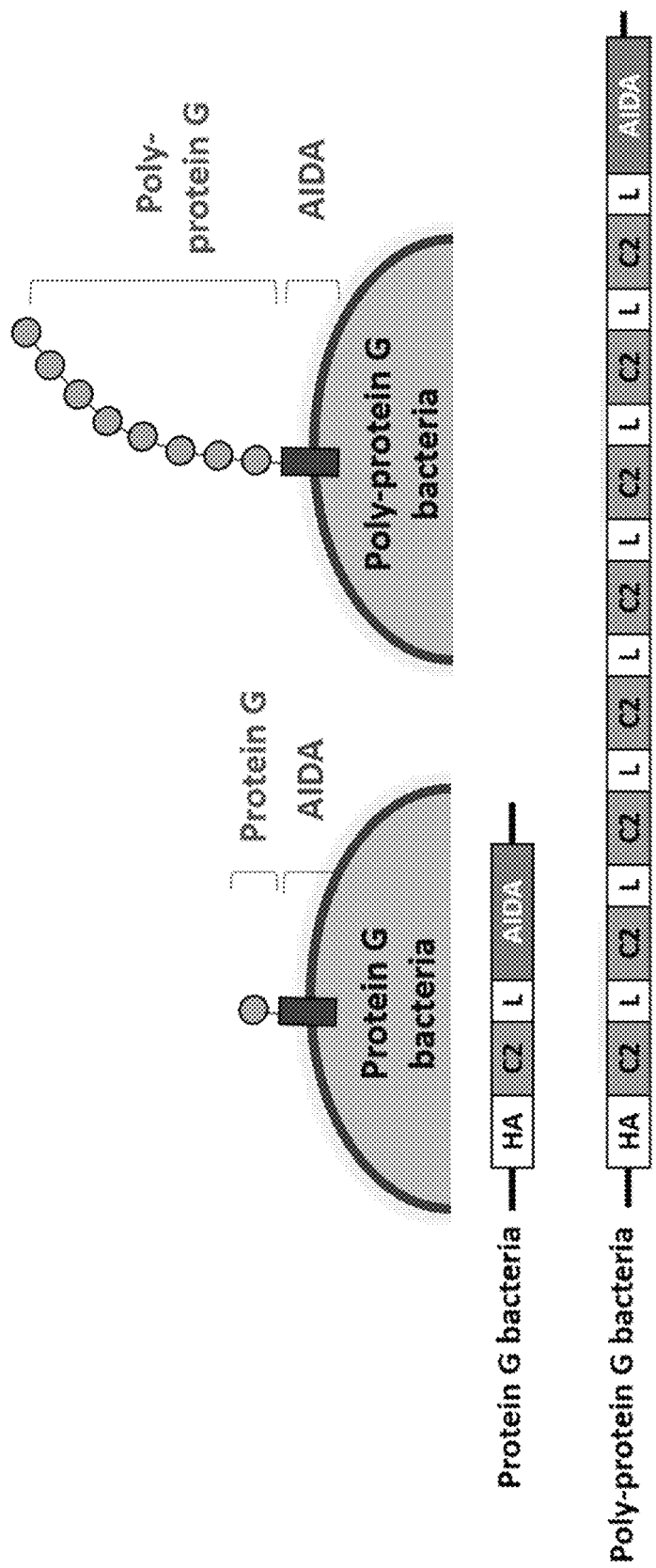
FIG. 5 shows the gene sequence of the poly-protein G of the invention, which is expressed on the membrane of the bacteria. For the protein G cell, the sequences include, from the N terminus to the C terminus, human influenza hemagglutinin (HA), protein G (C2), linker (L) and AIDA. For the poly-protein G cell, the sequences include, from the N terminus to the C terminus, HA, C2, L, C2, L, C2, L, C2, L, C2, L, C2, L, C2, L, C2, L and AIDA.

Example 2 Bacterial Cell Expressing the Tandemly Repeated Protein of the Invention (Poly Protein G) and its Antibody Capture Ability Construction of Poly Protein G The C2 domain of *Streptococcal* protein G was sequenced and cloned to produce one protein G-C2 domain and eight repeats of protein G-C2 domain. The autotransporter protein adhesin (AIDA) membrane protein was linked to the C-terminus of the resulting domains to form protein G-AIDA and poly-protein G-AIDA. The gene sequences from N- to C-terminus were HA-protein G-linker-AIDA and HA-poly-protein G-linker-AIDA, respectively (see FIG. 5).

Cell Line Stably Expressing the Poly-Protein G

Figure 6:
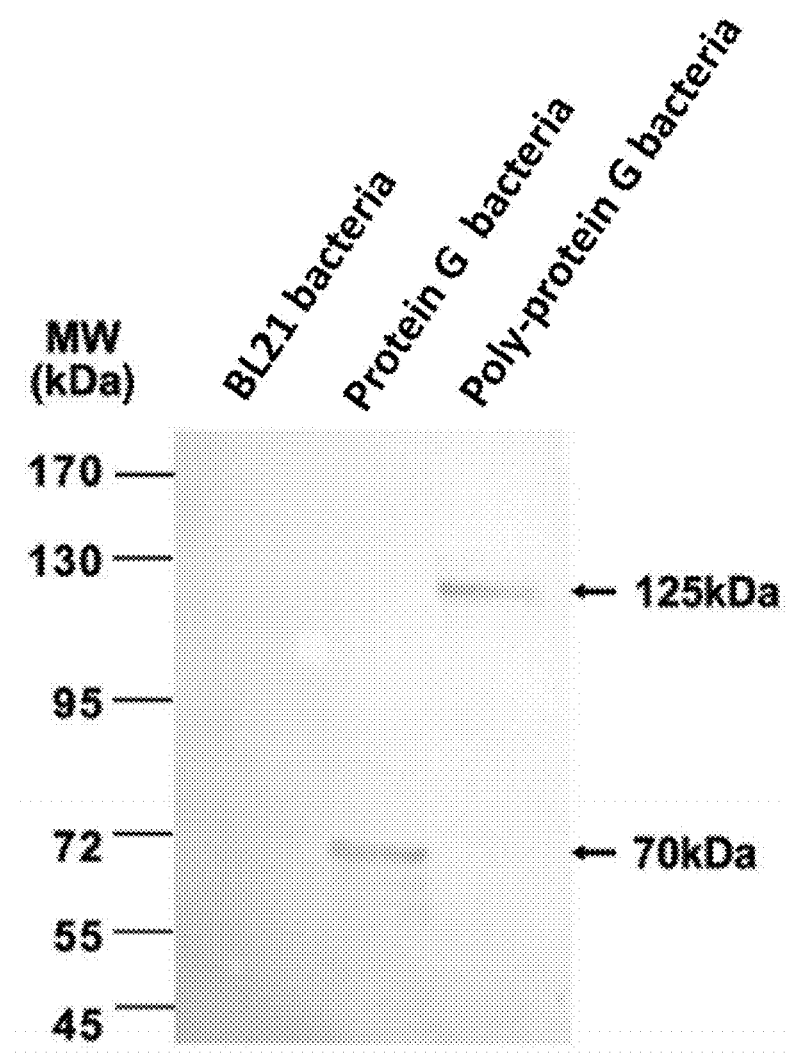
FIG. 6 shows the protein G expression in the protein G bacteria and the poly-protein G bacteria by Western blot. Lane 1: BL21 bacteria; Lane 2: protein G bacteria; and Lane 3: poly-protein G bacteria.

The gene sequences were inserted into vector pET22b to form pET22b-protein G-AIDA and pET22b-poly-protein G-AIDA, respectively and the resulting vectors were transformed into *E. coli* BL21 to form protein G bacteria and poly-protein G bacteria, respectively. The cell membrane proteins were collected and confirmed by western blot by adding anti-HA antibody and HRP Goat anti-mouse IgG Fcγantibody to confirm whether the protein G and the poly-protein G are correctly expressed. As shown in FIG. 6, protein-G-AIDA (molecule weight: 70 KDa) and poly-protein-G-AIDA (125 KDa) are correctly expressed on the membrane of the cells.

Capture of Antibody by Poly-Protein G Bacteria

Figure 7:
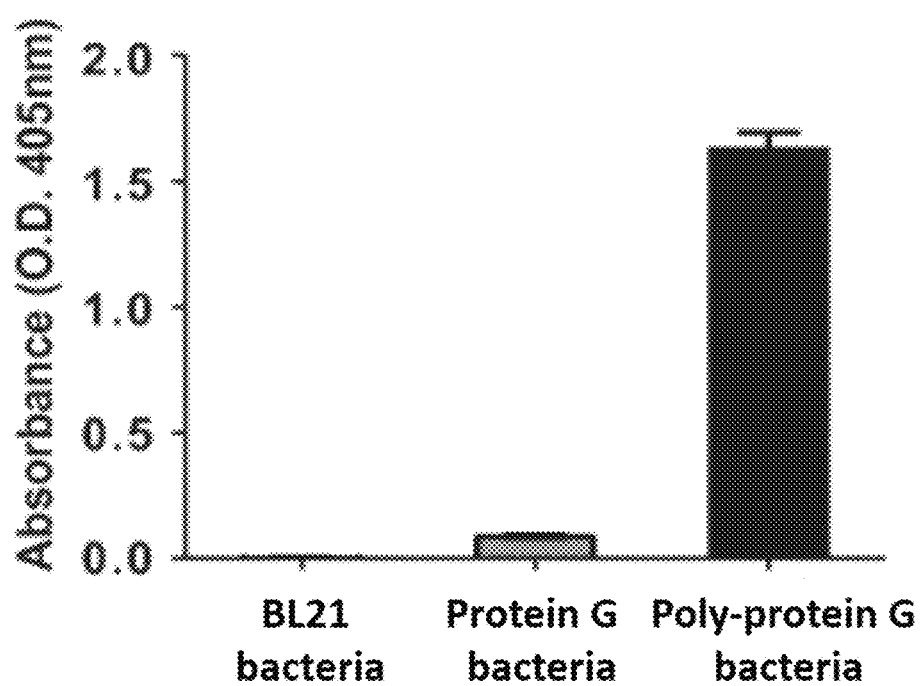
FIG. 7 shows the ability of the protein G bacteria and the poly-protein G bacteria in capturing the antibody.

The protein G bacteria and poly-protein G bacteria were immobilized on 96-well plates, respectively. 1 μg/mL Horseradish peroxidase (HRP)-conjugated goat anti-mouse IgG Fc antibody was added to the well and then ABTS was added for catalyzing the coloring. The resulting mixture was measured at O.D. 405 nm. At 1 μg/mL of antibody concentration, and the results show that the absorbance of the poly-protein G bacteria is 18.9 fold higher than that of the protein G bacteria (see FIG. 7).

Figure 8:
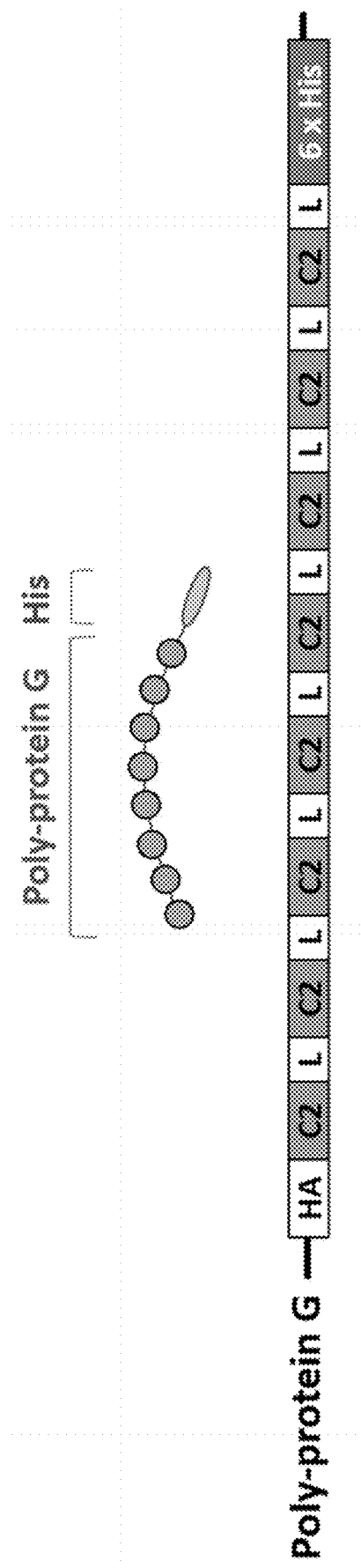
FIG. 8 shows the gene sequences of the poly-protein G of the invention. The sequences include, from the N terminus to the C terminus, HA, C2, L, C2, L, C2, L, C2, L, C2, L, C2, L, C2, L, C2, L and six histidines.

Example 3 Construction of Repeated Protein G (Poly-Protein G) and its Antibody Capture Ability Construction of Poly-Protein G Sequence The C2 domain of *Streptococcal* protein G was sequenced and cloned to produce an eight repeats of protein G-C2 domain. The histidine used as a identifier on protein purification was linked to the C-terminus of the resulting domain. The gene sequence from N- to C-terminus is HA-poly-protein G (see FIG. 8).

Mass Production of Poly-Protein G

Figure 9:
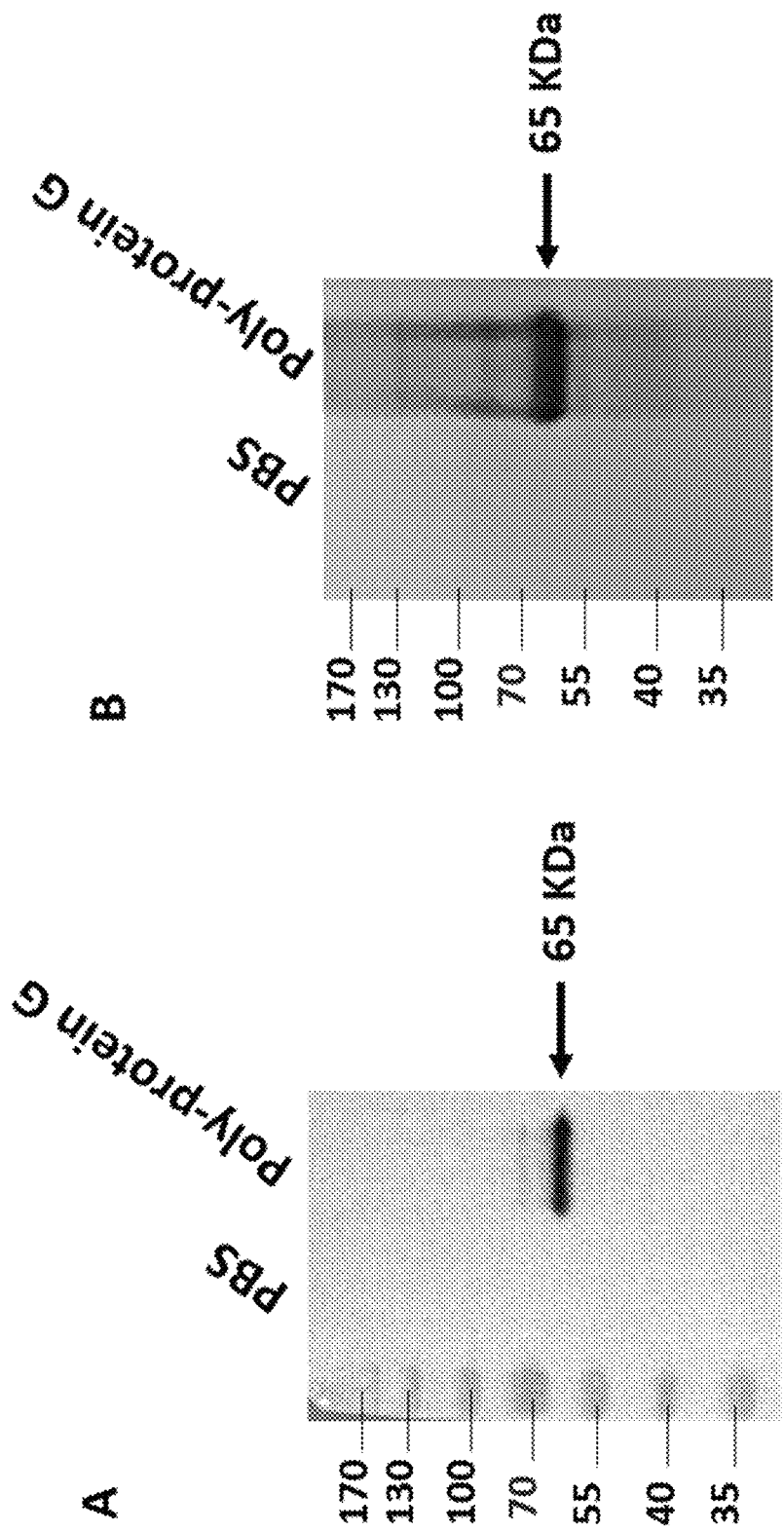
FIGS. 9 A and B show Western blot (A) and SDS-PAGE (B) of the poly-protein G. Lane 1: PBS as negative control; and Lane 2: poly-protein G.

To develop various kinds of poly-protein G used in immunoassay, repeated poly-protein G (eight repeats of C2 domain of protein G) was constructed and then inserted to a reverse viral vector pLNCX to form pLNCX-poly-protein-G. The resulting vector was transfected into Expi293 cells for protein mass production. The produced poly-protein G was purified by Ni affinity column and then confirmed by Western blot (FIG. 9 A) and 10% SDS-PAGE (non-reducing condition) (FIG. 9 B). The results show that the poly-protein G was correctly constructed and purified (65 KDa).

Capture of Antibody by Poly-Protein G

Figure 10:
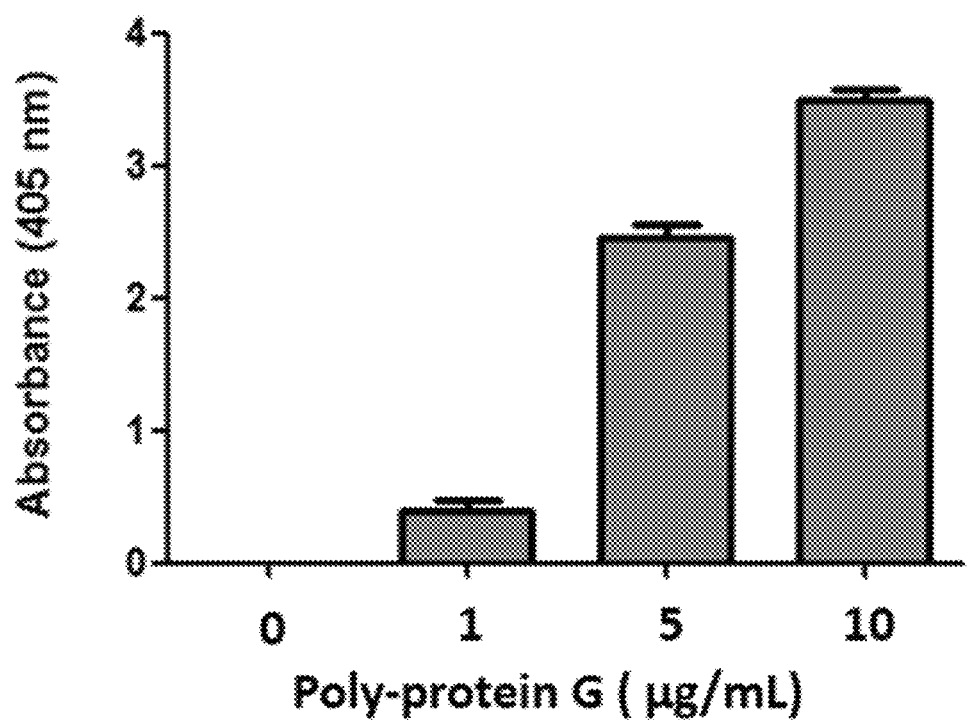
FIG. 10 shows the ability of the poly-protein G in capturing the antibody.

The poly-protein G in different concentrations (1 μg/mL, 5 μg/mL and 10 μg/mL) was immobilized on the 96-well plate and 1 μg/mL Horseradish peroxidase (HRP)-conjugated goat anti-mouse IgG Fc antibody was added to therein. Then ABTS was added for catalyzing the coloring. The resulting mixture was measured at O.D. 405 nm. At 1 μg/mL 5 μg/mL or 10 μg/mL of antibody concentration, and the results show that the poly-protein G can effectively capture the antibody and the amount of the captured antibody is increased in a concentration dependent manner (see FIG. 10).

Figure 11:
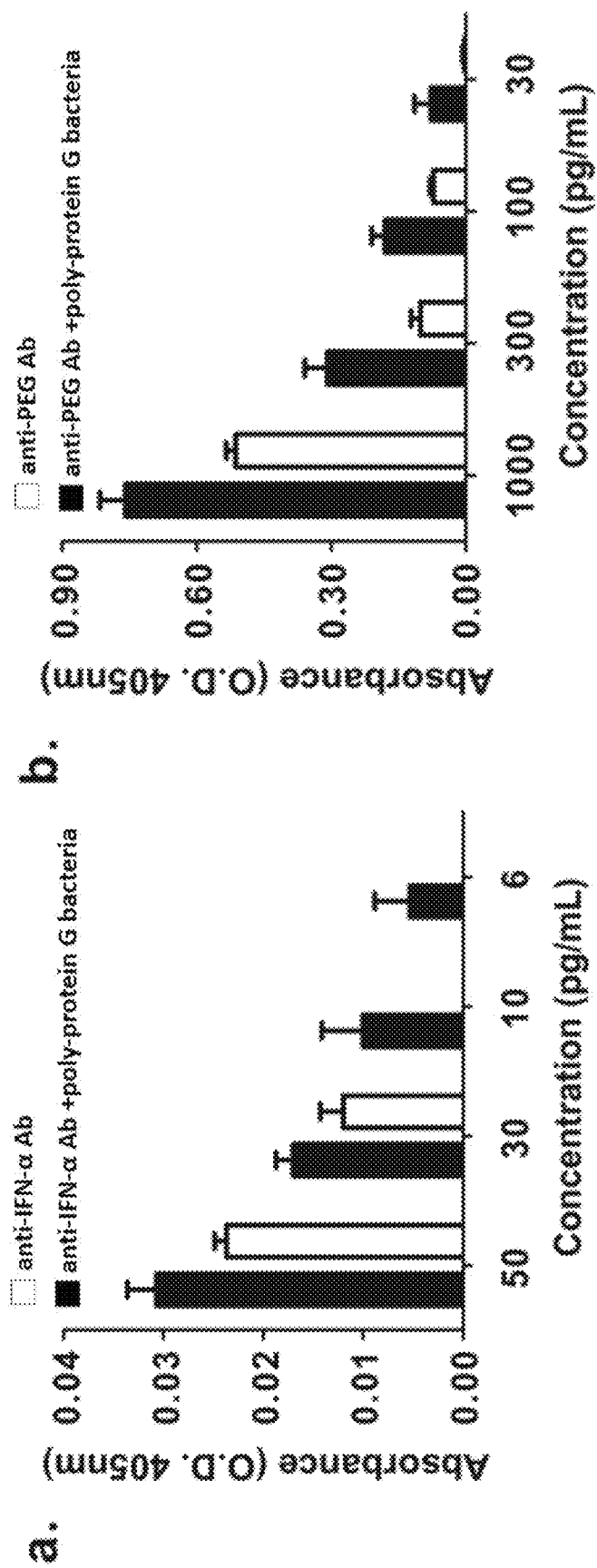
FIGS. 11 a and b show the sensitivity of detecting IFN-α (a) and PEGASYS (b) by using poly-protein G bacteria in sandwich ELISA (error bar: mean=/−SD).

Example 4 Poly-Protein G and Poly-Protein G Cell Greatly Increase Binding Amount of Detection Antibody to Antigen Site and Thus Increase Sensitivity of Immunoassay Increase of Detection Sensitivity of Sandwich ELISA by Poly-Protein G Bacteria 2 μg/mL MTI (an anti-IFN α Capture antibody) was added to ELISA plate and then 50 pg/mL, 30 pg/mL, 10 pg/mL and 6 pg/mL of IFN α were added thereto. The biotin conjugate MT2 (an anti-IFN-α Detection antibody) unbound or bound with the poly-protein G bacteria were added to the plate and then streptavidin-HRP and ABTS for coloring catalysis were added. The resulting mixture was measured at O.D. 405 nm. The results show that the absorbance of the detection antibody bound with the poly-protein G bacteria is much higher than that of the detection antibody unbound with the poly-protein G and thus the sensitivity of the sandwich ELISA in detection of IFN α can be increased (see FIG. 11 *a*).

1 μg/mL AGP4 (an anti-PEG capture antibody, IgM type) was added to ELISA plate and then 1000 pg/mL, 300 pg/mL, 100 pg/mL and 30 pg/mL of PEGASYS (a PEG modified protein drug) were added thereto. The biotin conjugate 3.3 (an anti-PEG Detection antibody, IgG type) unbound or bound with the poly-protein G bacteria were added to the plate and then streptavidin-HRP and ABTS for coloring catalysis were added. The resulting mixture was measured at O.D. 405 nm. The results show that the absorbance of the detection antibody bound with the poly-protein G bacteria is much higher than that of the detection antibody unbound with the poly-protein G bacteria and thus the sensitivity of the sandwich ELISA in detection of PEGASYS can be increased (see FIG. 11*b*).

Increase of Detection Sensitivity of Sandwich ELISA by Poly-Protein G

Figure 12:
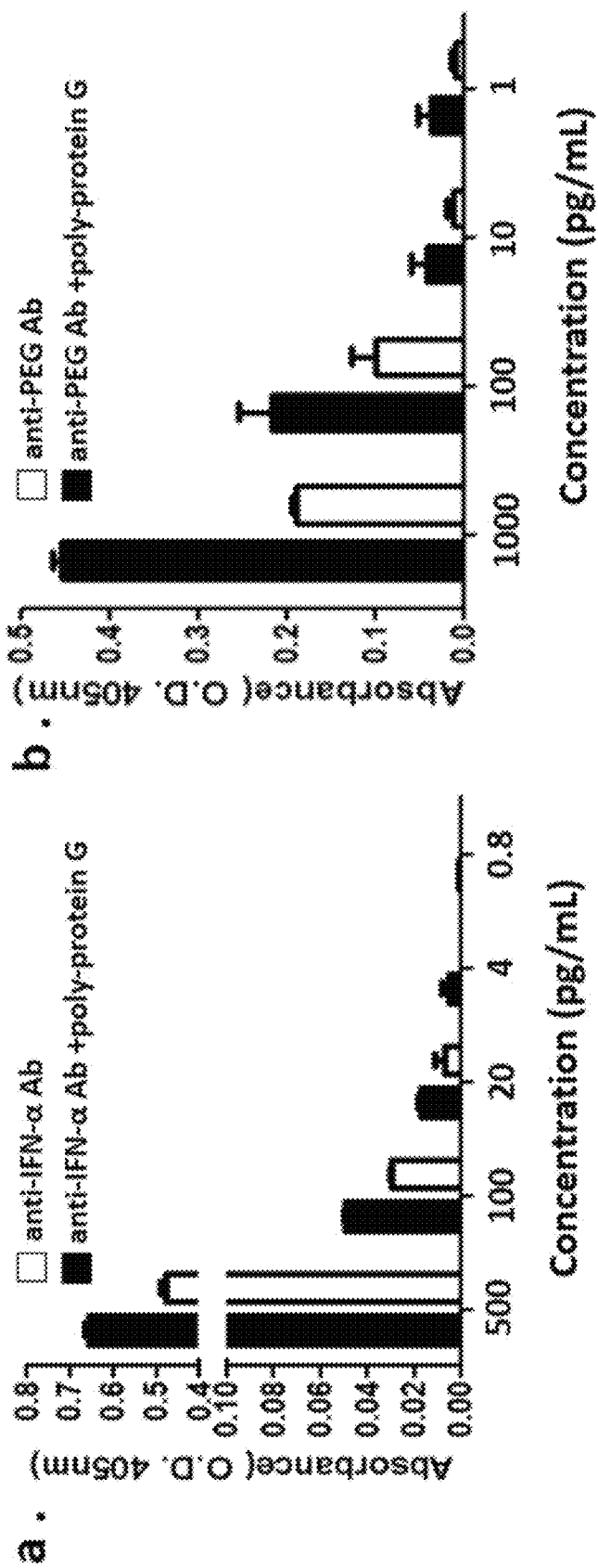
FIGS. 12 a and b show the sensitivity of detecting IFN-α (a) and PEGASYS (b) by using poly-protein G in sandwich ELISA (error bar: mean=/−SD).

2 μg/mL MTI (an anti-IFN α capture antibody) was added to ELISA plate and then 500 pg/mL, 100 pg/mL, 20 pg/mL, 4 pg/mL and 0.8 pg/mL of IFN α were added thereto. The biotin conjugate MT2 (an anti-IFN-α detection antibody) unbound or bound with the poly-protein G was added to the plate and then streptavidin-HRP and ABTS for coloring catalysis were added. The resulting mixture was measured at O.D. 405 nm. The results show that the absorbance of the detection antibody bound with the poly-protein G is much higher than that of the detection antibody unbound with the poly-protein G and thus the sensitivity of the sandwich ELISA in detection of IFN α can be increased (see FIG. 12 *a*).

1 μg/mL AGP4 (an anti-PEG capture antibody, IgM type) was added to ELISA plate and then 1000 pg/mL, 100 pg/mL, 10 pg/mL and 1 pg/mL of PEGASYS (a PEG modified protein drug) were added thereto. The biotin conjugate 3.3 Ab (an anti-PEG detection antibody, IgG type) unbound or bound with the poly-protein G were added to the plate and then streptavidin-HRP and ABTS for coloring catalysis were added. The resulting mixture was measured at O.D. 405 nm. The results show that the absorbance of the detection antibody bound with the poly-protein G is much higher than that of the detection antibody unbound with the poly-protein G and thus the sensitivity of the sandwich ELISA in detection of PEGASYS can be increased (see FIG. 12 *b*).

Figure 13:
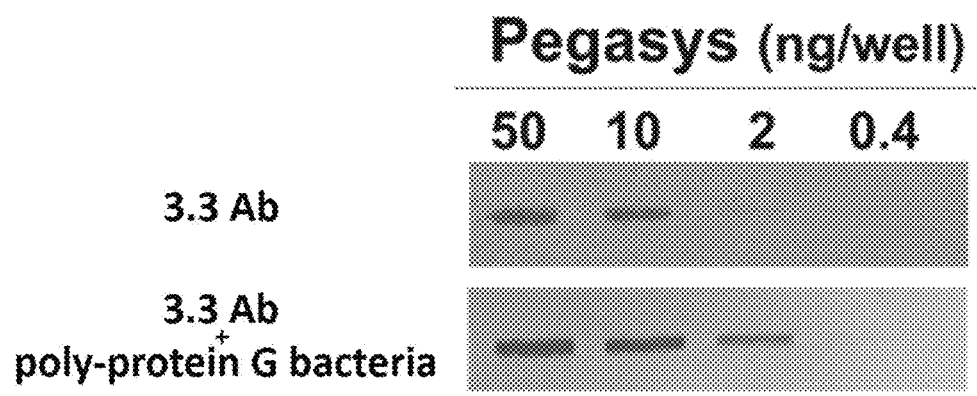
FIG. 13 shows that the poly-protein G bacterium increases sensitivity and improve detection limit of Western Blot.

Increase of Detection Sensitivity of Western Blot by Poly-Protein G Bacteria 50 ng/well, 10 ng/well, 2 ng/well and 0.4 ng/well of PEGASYS (a PEG modified protein drug) were subjected to 10% (w/v) SDS-PAGE electrolysis and then blotted on the nitrocellulose membrane. 2 μg/mL of 3.3Ab (an anti-PEG Detection antibody, IgG type) unbounded or bounded with the poly-protein G bacteria was added to the membrane and then HRP-conjugated goat anti-mouse antibody was added for coloring. The results show that the detection limit of the 3.3 Ab bounded with the poly-protein G bacteria for PEGASYS was enhanced to 0.4 ng/well, while the sensitivity of the 3.3 Ab unbounded with the poly-protein G bacteria was 10 ng/well (see FIG. 13). The results show that the poly-protein G bacteria indeed can increase the sensitivity and improve the detection limit of Western blot.

Figure 14:
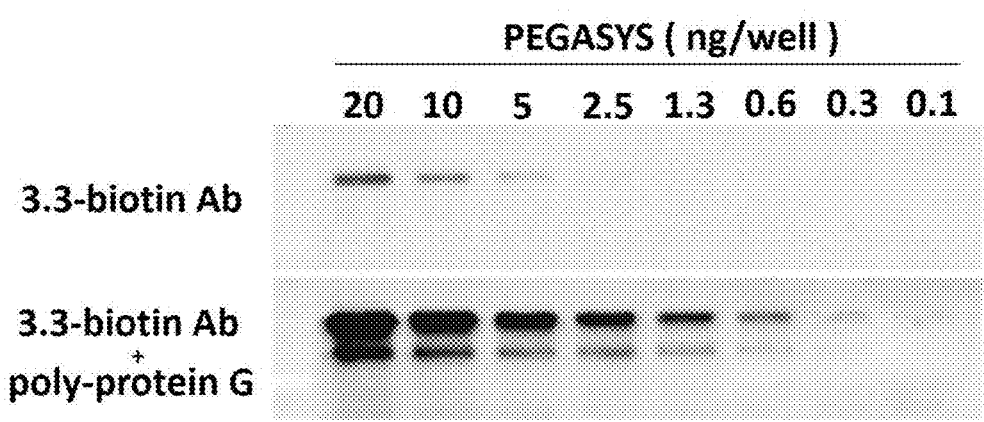
FIG. 14 shows that the poly-protein G increases sensitivity and improve detection limit of Western Blot.

Increase of Detection Sensitivity of Western Blot by Poly-Protein G 20 ng/well, 10 ng/well, 5 ng/well, 2.5 ng/well, 1.3 ng/well, 0.6 ng/well, 0.3 ng/well and 0.1 ng/well of PEGASYS (a PEG modified protein drug) were subjected to 10% (w/v) SDS-PAGE electrolysis and then blotted on the nitrocellulose membrane. 2 μg/mL of the biotin conjugated 3.3Ab (an anti-PEG Detection antibody, IgG type) unbounded or bounded with the poly-protein G was added to the membrane and then streptavidin-HRP was added for coloring. The results show that the detection limit of the biotin-3.3 Ab bounded with the poly-protein G for PEGASYS was enhanced to 0.1 ng/well, while the sensitivity of the biotin-3.3 Ab unbounded with the poly-protein G was 2.5 ng/well (see FIG. 14). The results show that the poly-protein G indeed can increase the sensitivity and improve the detection limit of Western blot.

Figure 15:
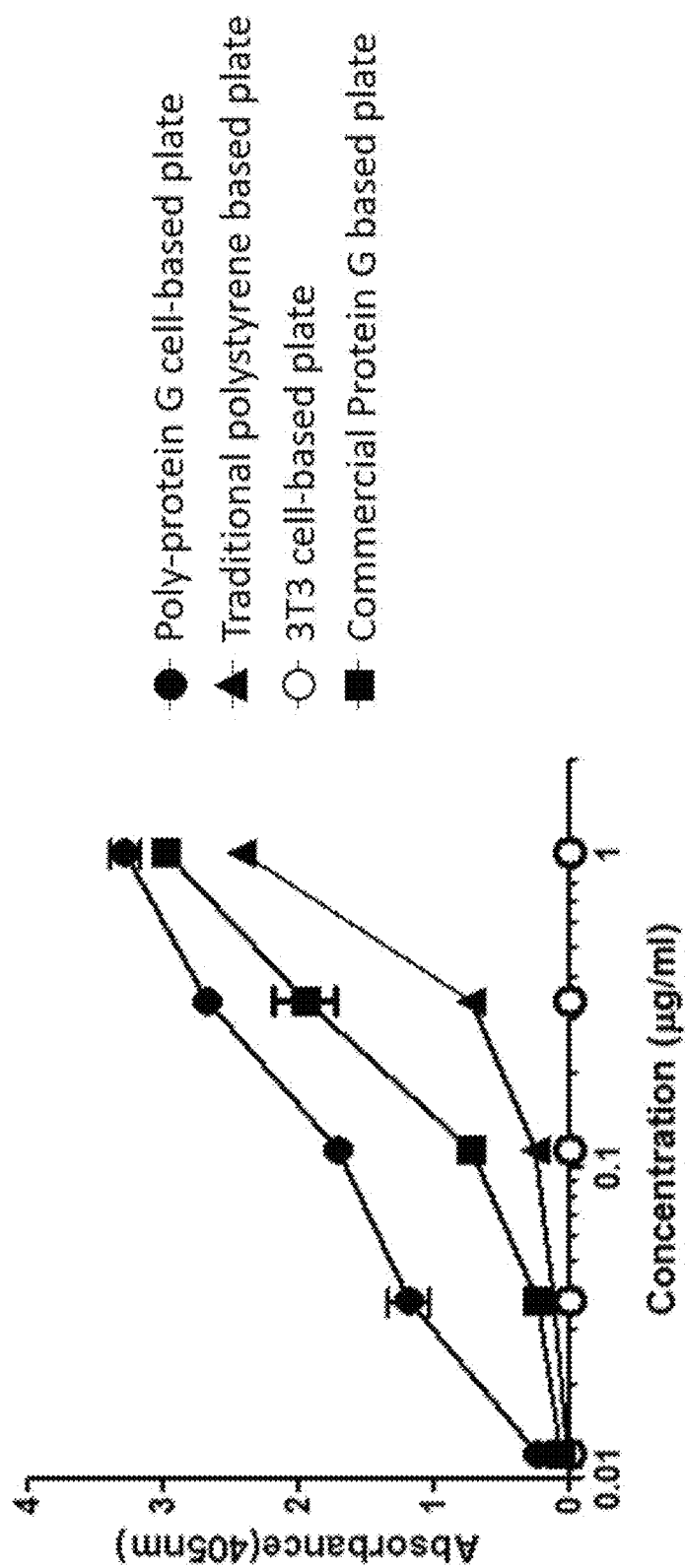
FIG. 15 shows the capture antibody loading amounts of the poly-protein G cell-based plate, the traditional polystyrene-based plate and the commercial protein G-based plate (error bar: mean=/−SD).

Example 5 Poly-Protein G-Based Plate and Poly-Protein G Cell-Based Plate Increase the Loading Amount of Capture Antibody Increase of Loading Amounts of Capture Antibody by Poly-Protein G Cell-Based Plate The poly-protein G cells were immobilized on the plate to produce the poly-protein G cell-based plate. 0.0123 μg/mL, 0.0371 μg/mL, 0.11 μg/mL, 0.33 μg/mL and 1 μg/mL of biotin-3.3Ab (an anti-PEG Capture antibody, IgG type) were added to the poly-protein G cell-based plate, traditional polystyrene-based plate and the commercial protein G-based plate, respectively. Then streptavidin-HRP and ABTS for coloring catalysis were added to the plates. The resulting mixtures were measured at O.D. 405 nm. The results show that at 0.0123 μg/mL, 0.0371 μg/mL, 0.11 μg/mL, 0.33 μg/mL and 1 μg/mL of biotin-3.3Ab, the antibody amounts loaded at the poly-protein G cell-based plate are 18, 9.5, 6, 3.5 and 1.8 times higher than those of the traditional polystyrene-based plate, respectively, and 3.5, 5.1, 2.4, 1.3 and 1.1 times higher than those of the commercial protein G-based plate, respectively. The results show that the antibody amounts loaded at the poly-protein G cell-based plate are much higher than those at the traditional polystyrene-based plate and the commercial protein G-based plate (see FIG. 15).

Increase of Loading Amounts of Capture Antibody by Poly-Protein G-Based Plate

Figure 16:
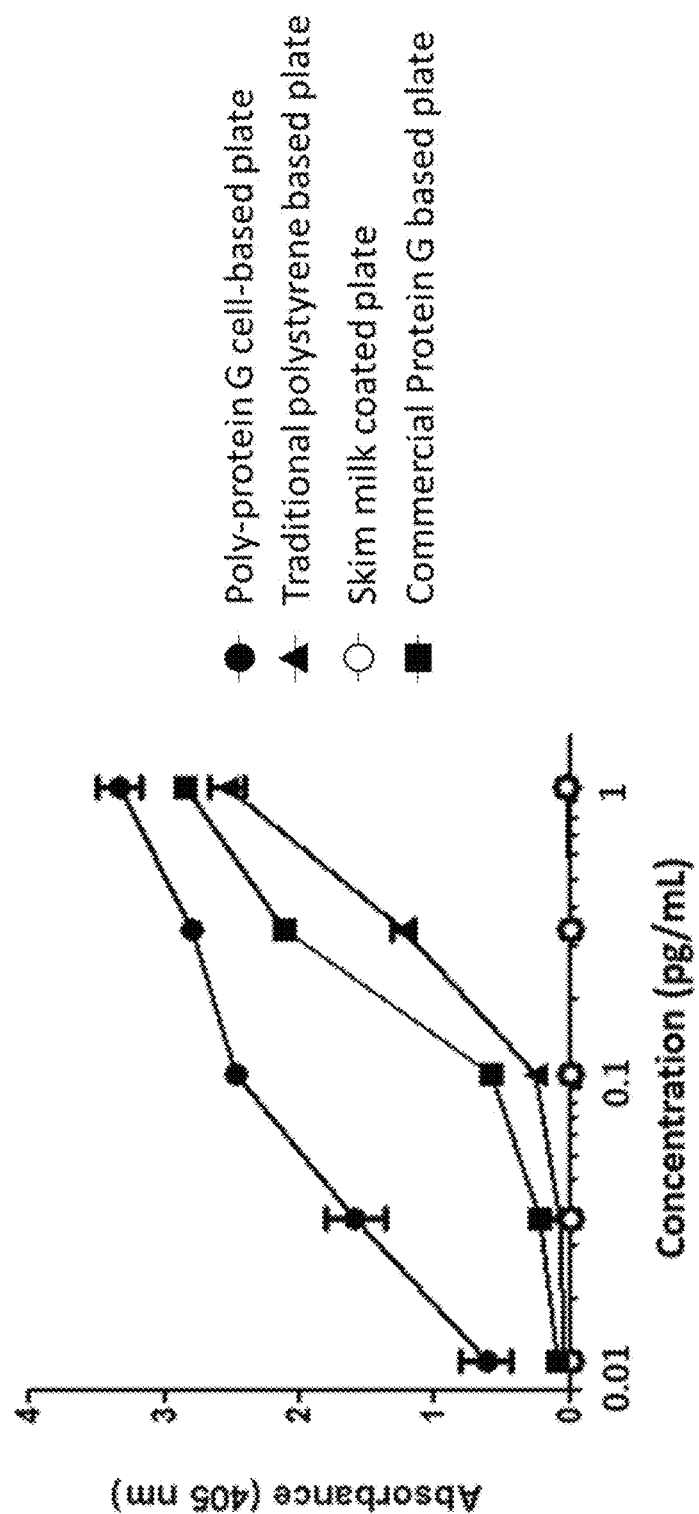
FIG. 16 shows the capture antibody loading amounts of the poly-protein G-based plate, traditional polystyrene-based plate and the commercial protein G-based plate (error bar: mean=/−SD).

The poly-proteins G were immobilized on the plate to produce the poly-protein G-based plate. 0.0123 μg/mL, 0.0371 μg/mL, 0.11 μg/mL, 0.33 μg/mL and 1 μg/mL of biotin-3.3Ab were added to the poly-protein G-based plate, traditional polystyrene-based plate and the commercial protein G-based plate, respectively. Then streptavidin-HRP and ABTS for coloring catalysis were added to the plates. The resulting mixtures were measured at O.D. 405 nm. The results show that at 0.0123 μg/mL, 0.0371 μg/mL, 0.11 μg/mL, 0.33 μg/mL and 1 μg/mL of biotin-3.3Ab, the antibody amounts loaded at the poly-protein G-based plate are 14, 20, 10, 2.2 and 1.3 times higher than those of the traditional polystyrene-based plate, respectively, and 7.8, 5.8, 4, 1.3 and 1.15 times higher than those of the commercial protein G-based plate, respectively. The results show that the antibody amounts loaded at the poly-protein G-based plate are much higher than those at the traditional polystyrene-based plate and the commercial protein G-based plate (see FIG. 16).

Figure 17:
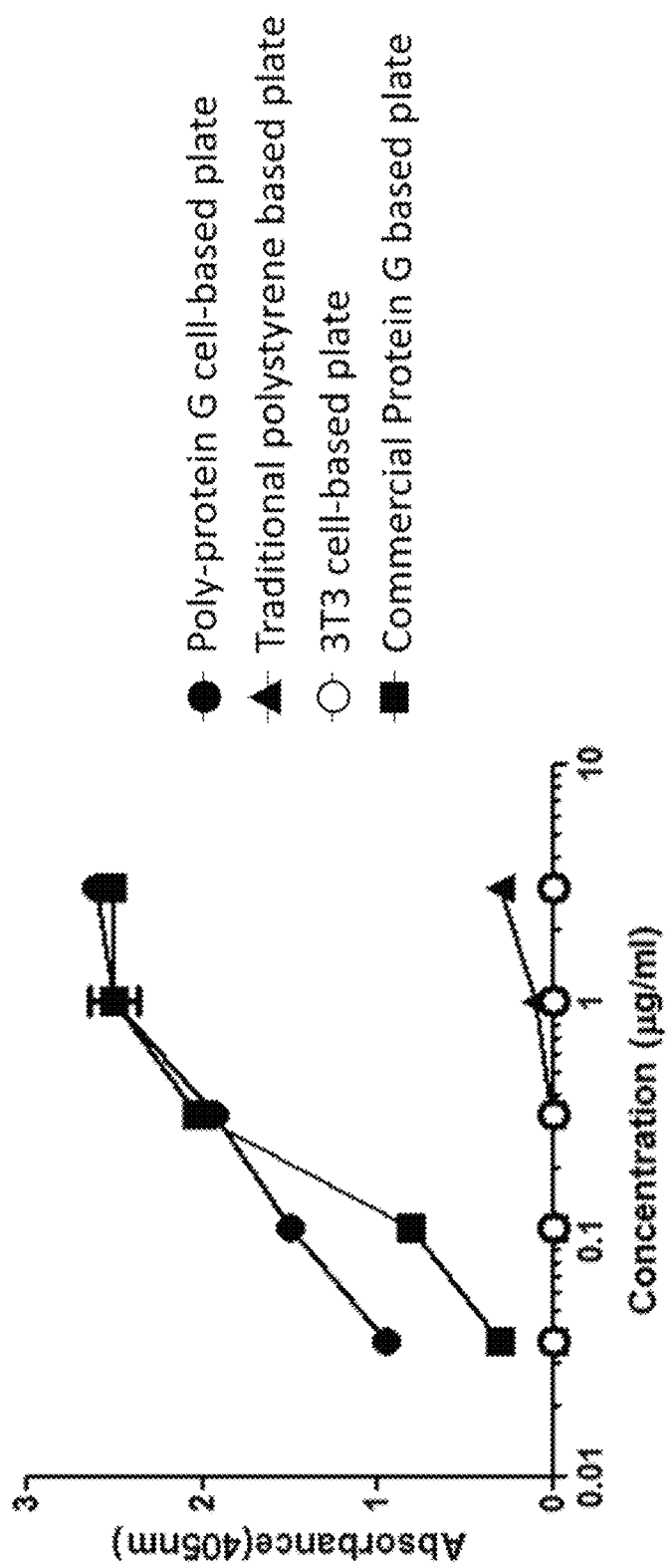
FIG. 17 shows, at the same CTLA4-biotin concentration, the CTLA4-biotin binding amounts of the poly-protein G cell-based plate, the traditional polystyrene-based plate and the commercial protein G-based plate capturing serial diluted anti-CTLA4 antibody (error bar: mean=/−SD).

Example 6 Poly-Protein G Cell-Based Plate Increase the Binding Amounts of Various Antigen Analytes Increase of Binding Amounts of CTL4 Antigen by Poly-Protein G Cell-Based Plate 0.0371 μg/mL, 0.11 μg/mL, 0.33 μg/mL, 1 μg/mL and 3 μg/mL of anti-CTLA4 antibody were added to the poly-protein G cell-based plate, the traditional polystyrene-based plate and the commercial protein G-based plate, respectively. 1 μg/mL of CTLA4-biotin, streptavidin-HRP and ABTS for coloring catalysis were sequentially added to the plates. The resulting mixtures were measured at O.D. 405 nm. The results show that at 0.0371 μg/mL, 0.11 μg/mL, 0.33 μg/mL, 1 μg/mL and 3 μg/mL of the anti-CTLA4 antibody, the amount of CTLA4-biotin bound to the anti-CTLA4 antibody in the poly-protein G cell-based plate is much higher than that of the traditional polystyrene-based plate. At 0.0371 μg/mL and 0.11 μg/mL of the anti-CTLA4 antibody, the amount of CTLA4-biotin bound to the anti-CTLA4 antibody in the poly-protein G cell-based plate is much higher than that of the commercial protein G-based plate (see FIG. 17).

Figure 18:
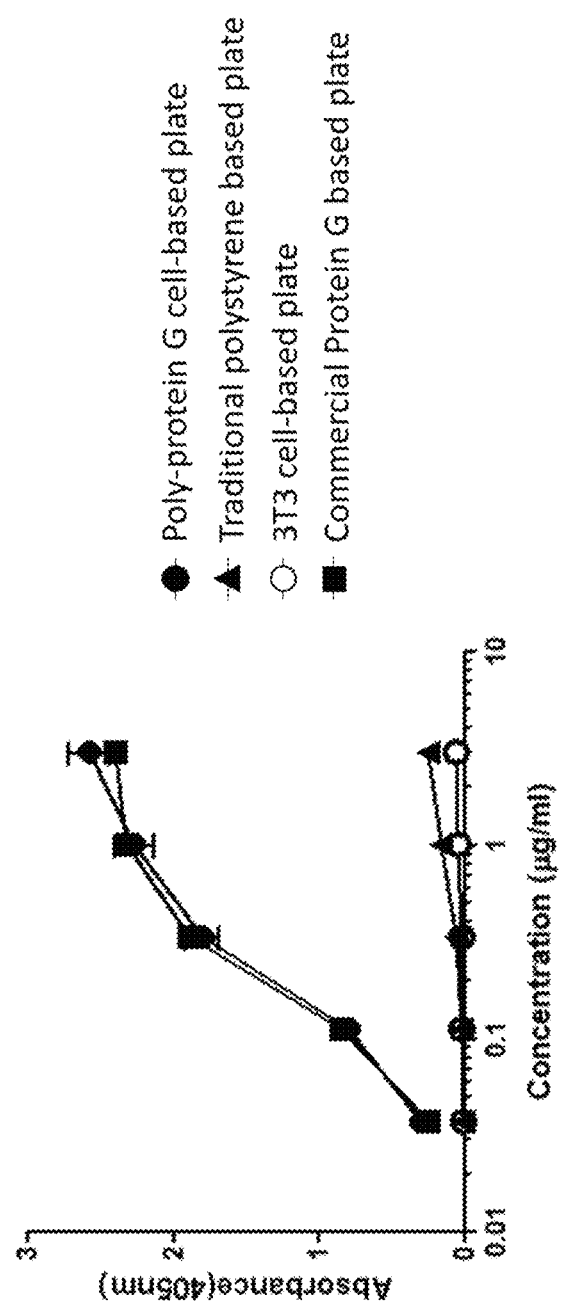
FIG. 18 shows that, at the serial diluted CTLA4-biotin concentration, CTLA4-biotin binding amounts of the poly-protein G cell-based plate, the traditional polystyrene-based plate and the commercial protein G-based plate capturing high concentration of anti-CTLA4 antibody (error bar: mean=/−SD).
Figure 19:
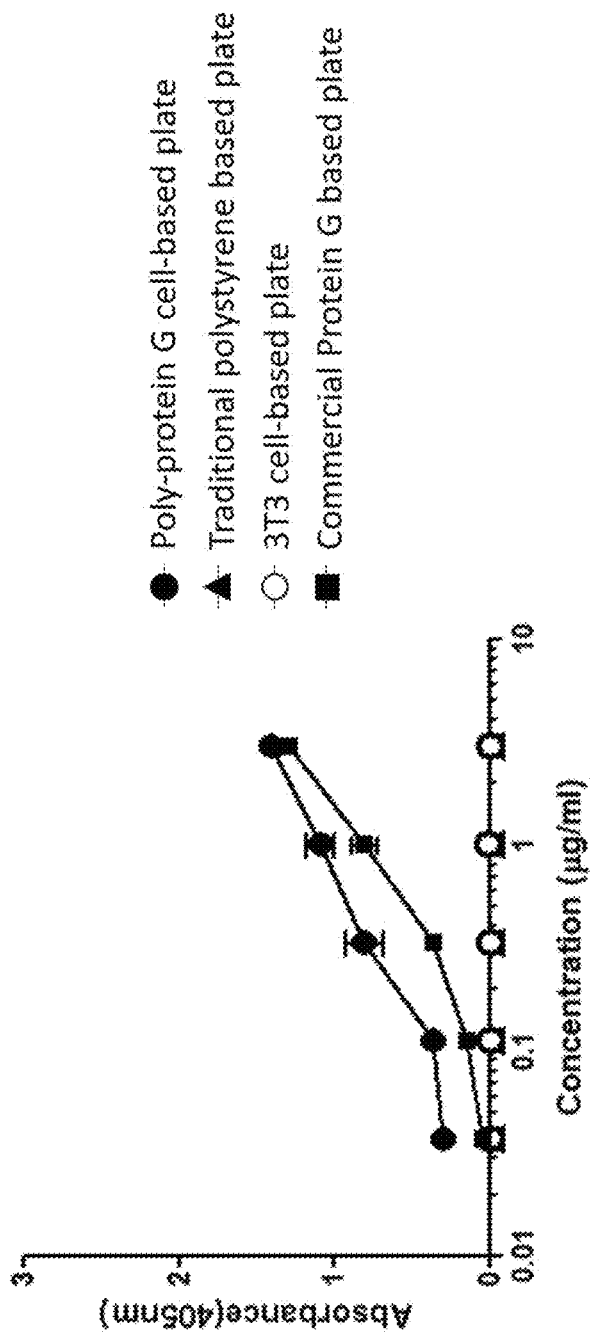
FIG. 19 shows that, at the serial diluted CTLA4-biotin concentration, CTLA4-biotin binding amounts of the poly-protein G cell-based plate, the traditional polystyrene-based plate and the commercial protein G-based plate capturing low concentration of anti-CTLA4 antibody (error bar: mean=/−SD).

1 μg/mL or 0.1 μg/mL of the anti-CTLA4 antibody was added to the poly-protein G cell-based plate, the traditional polystyrene-based plate and the commercial protein G-based plate, respectively. Then, 0.0371 μg/mL, 0.11 μg/mL, 0.33 μg/mL, 1 μg/mL and 3 μg/mL of the CTLA4-biotin were added to the plate, respectively. Streptavidin-HRP and ABTS for coloring catalysis were sequentially added to the plates. The resulting mixtures were measured at O.D. 405 nm. The results show that at the high concentration (1 μg/mL) of the anti-CTLA4 antibody, the amounts of the CTLA4-biotin (0.0371 μg/mL, 0.11 μg/mL, 0.33 μg/mL, 1 μg/mL and 3 μg/mL of) bound to the anti-CTLA4 antibody in the poly-protein G cell-based plate are similar to that of the commercial protein G-based plate, but are much higher than that of the traditional polystyrene-based plate (see FIG. 18). However, at the at the low concentration (0.1 μg/mL) of the anti-CTLA4 antibody, the amounts of the CTLA4-biotin (0.0371 μg/mL, 0.11 μg/mL, 0.33 μg/mL, 1 μg/mL and 3 μg/mL of) bound to the anti-CTLA4 antibody in the poly-protein G cell-based plate are 6.5, 2.4, 2.2, 1.3 and 1.1 times higher than that of the commercial protein G-based plate, whereas no anlayte can be detected by the traditional polystyrene-based plate (see FIG. 19).

Figure 20:
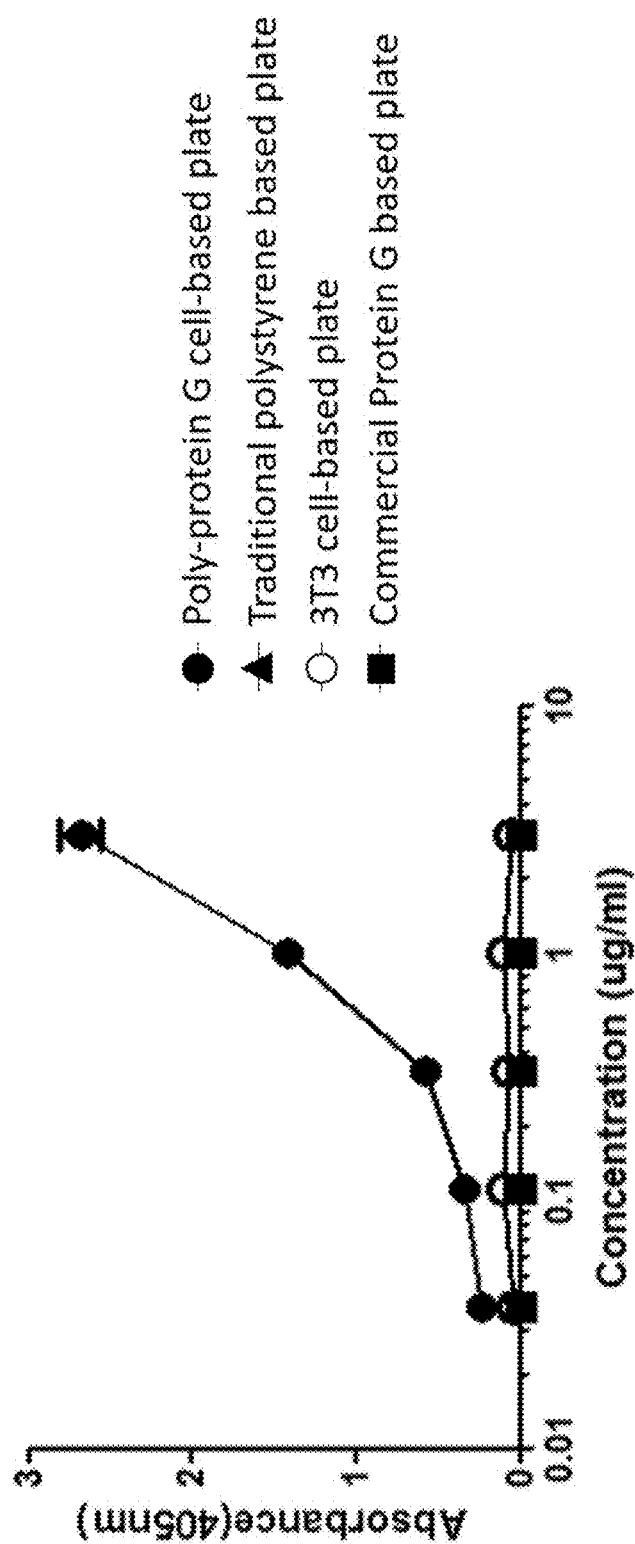
FIG. 20 shows, at the same PEG5K-biotin concentration, the PEG5K-biotin binding amounts of the poly-protein G cell-based plate, the traditional polystyrene-based plate and the commercial protein G-based plate capturing the serial diluted anti-PEG antibody (error bar: mean=/−SD).

Increase of Binding Amounts of PEG-Biotin by Poly-Protein G Cell-Based Plate 0.0371 μg/mL, 0.11 μg/mL, 0.33 μg/mL, 1 μg/mL and 3 μg/mL of 3.3 Ab (an anti-PEG Capture antibody, IgG type) were added to the poly-protein G cell-based plate, the traditional polystyrene-based plate and the commercial protein G-based plate, respectively. 1 μg/mL of PEGSK-biotin, streptavidin-HRP and ABTS for coloring catalysis were sequentially added to the plates. The resulting mixtures were measured at O.D. 405 nm. The results show that at 0.0371 μg/mL, 0.11 μg/mL, 0.33 μg/mL, 1 μg/mL and 3 μg/mL of the anti-PEG antibody, the amount of PEGSK-biotin (1 μg/mL) bound to the anti-PEG antibody in the poly-protein G cell-based plate is much higher than that of the commercial protein G-based plate and that of the traditional polystyrene-based plate (see FIG. 20).

Increase of Binding Amounts of PEG2K-LIPODOX by Poly-Protein G Cell-Based Plate

Figure 21:
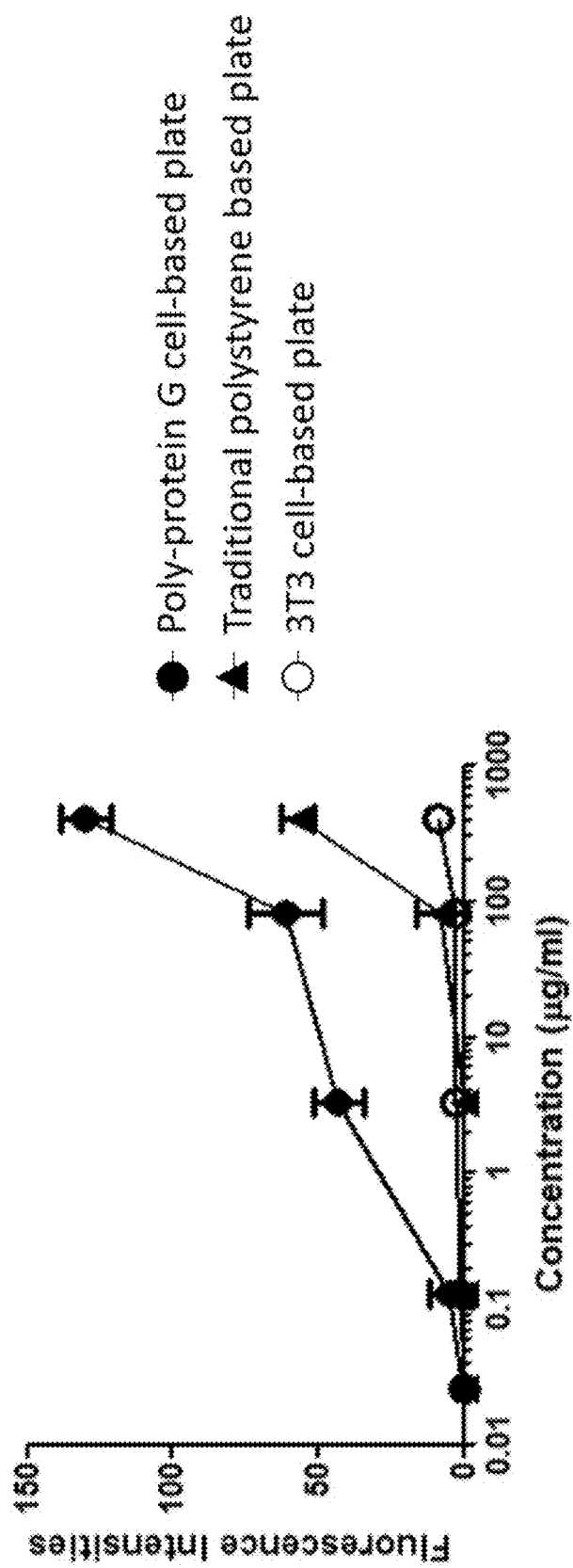
FIG. 21 shows, at the serial diluted PEG2K-LIPODOX concentration, the 2K-LIPODOX binding amounts of the poly-protein G cell-based plate and the traditional polystyrene-based plate capturing anti-PEG antibody (error bar: mean=/−SD).

1 μg/mL of 3.3 Ab (an anti-PEG Capture antibody, IgG type) was added to the poly-protein G cell-based plate and the traditional polystyrene-based plate, respectively. 0.0256 μg/mL, 0.128 μg/mL, 3.2 μg/mL, 80 μg/mL and 400 μg/mL of PEG2K-LIPODOX were added to the plates, respectively. The binding amounts of PEG2K-LIPODOX to the poly-protein G cell-based plate and the traditional polystyrene-based plate were measured by fluorescent analyzer. The results show that the amounts of PEG2K-LIPODOX bound to the anti-PEG antibody in the poly-protein G cell-based plate are much higher than that of the traditional polystyrene-based plate (see FIG. 21).

Figure 22:
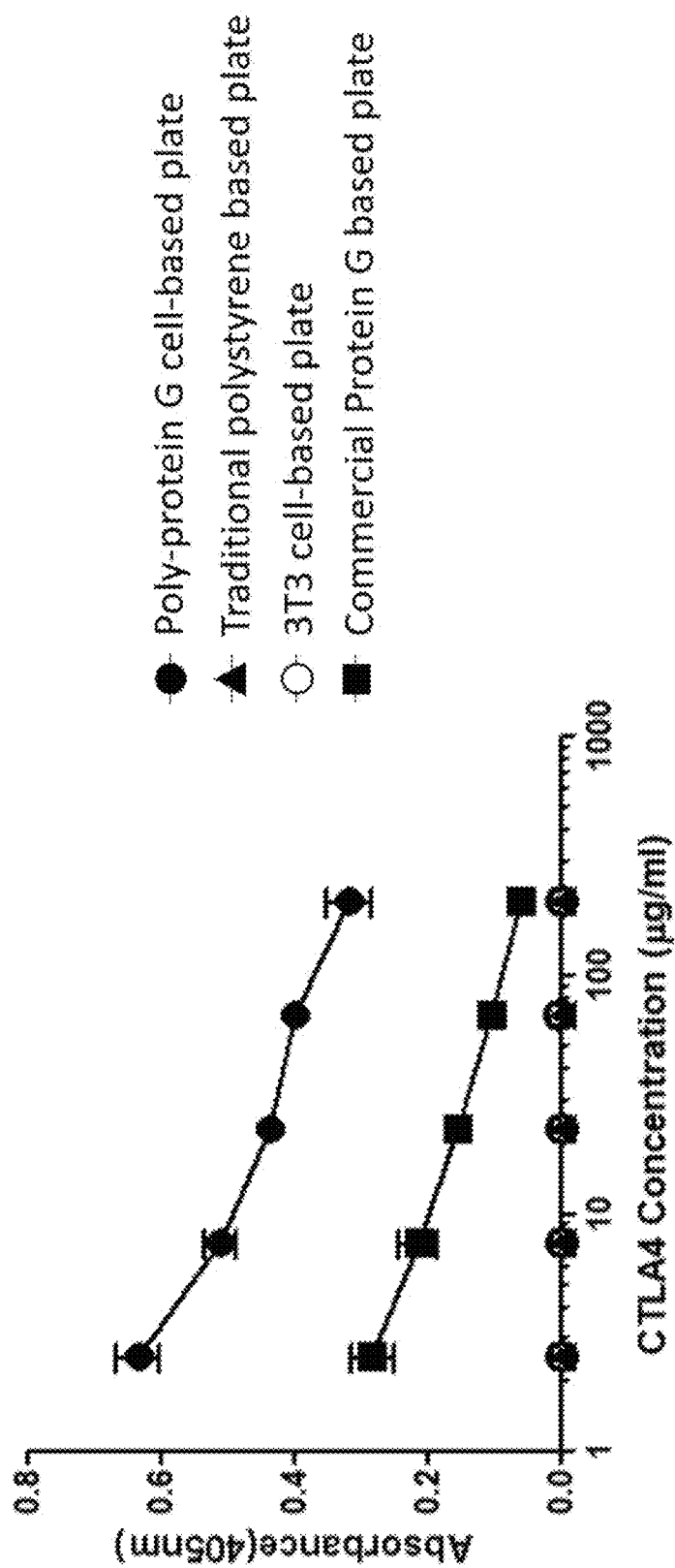
FIG. 22 shows the detection sensitivity of CTLA4 by the poly-protein G cell-based plate, the traditional polystyrene-based plate and the commercial protein G-based plate in competition ELISA (error bar: mean=/−SD).

Example 7 Poly-Protein G Cell-Based Plate Greatly Increase Sensitivity of Competition ELISA 0.1 μg/mL of the anti-CTLA4 antibody was added to the poly-protein G cell-based plate, the traditional polystyrene-based plate and the commercial protein G-based plate, respectively. The CTL4 analyte and CTLA4-Biotin were added to the plates to competitively bind to the binding site of the anti-CTLA4 antibody. Streptavidin-HRP and ABTS were then added to the plate. The resulting mixtures were measured at O.D. 405 nm. The results show that the poly-protein G cell-based plate indeed can detect the CTL4 analyte and the absorbance intensity of the poly-protein G cell-based plate is much higher than the traditional polystyrene-based plate, whereas the traditional polystyrene-based plate cannot detect the CTLA4 (FIG. 22).

Figure 23:
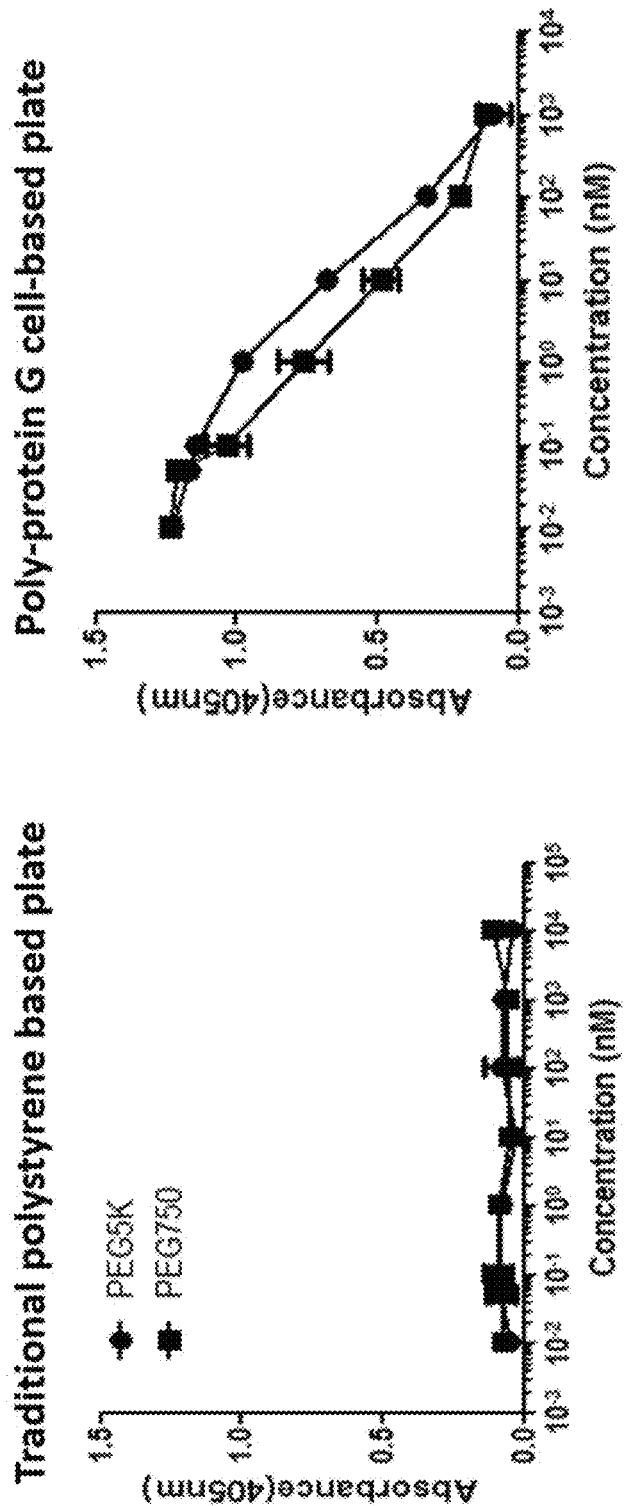
FIG. 23 shows the detection sensitivity of the PEG 5K and PEG750 by the poly-protein G cell-based plate and the traditional polystyrene-based plate in competition ELISA (error bar: mean=/−SD).

1 µg/mL of the anti-PEG antibody was added to the poly-protein G cell-based plate and the traditional polystyrene-based plate, respectively. The PEG analyte and PEG-biotin were added to the plates to competitively bind to the binding site of the anti-PEG antibody. Streptavidin-HRP and ABTS were then added to the plate. The resulting mixtures were measured at O.D. 405 nm. The results show that the poly-protein G cell-based plate can detect PEGSK and PEG750 at 0.01 nM (FIG. 23, right), whereas the traditional polystyrene-based plate cannot detect the PEG (FIG. 23, left).

Figure 24:
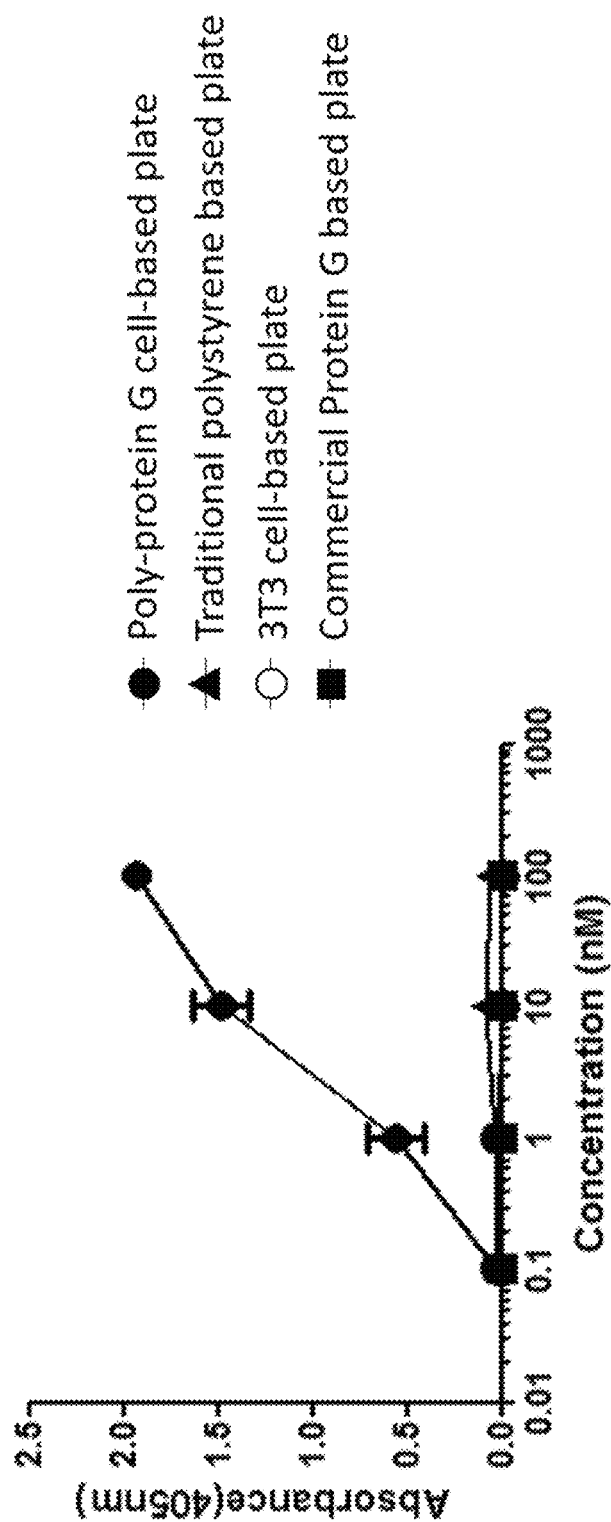
FIG. 24 shows the detection sensitivity of the PEG10K by the poly-protein G cell-based plate, the traditional polystyrene-based plate and the commercial protein G-based plate in sandwich ELISA (error bar: mean=/−SD).

Example 8 Poly-Protein G Cell Plate Greatly Increase Sensitivity of Sandwich ELISA 1 µg/mL of 15.2 Ab (an anti-PEG antibody, IgG type) was added to the poly-protein G cell-based plate, the traditional polystyrene-based plate and the commercial protein G-based plate, respectively. 0.1 nM, 1 nM, 10 nM and 100 nM of PEG10K were added to the plates. AGP4-biotin (a biotin conjugated anti-PEG Detection antibody, IgM type), Streptavidin-HRP and ABTS were sequentially added to the plate. The resulting mixtures were measured at O.D. 405 nm. The results show that the poly-protein G cell-based plate can detect PEG10K, whereas the traditional polystyrene-based plate and the commercial protein G-based plate cannot effectively detect PEG10K (FIG. 24).

Figure 25:
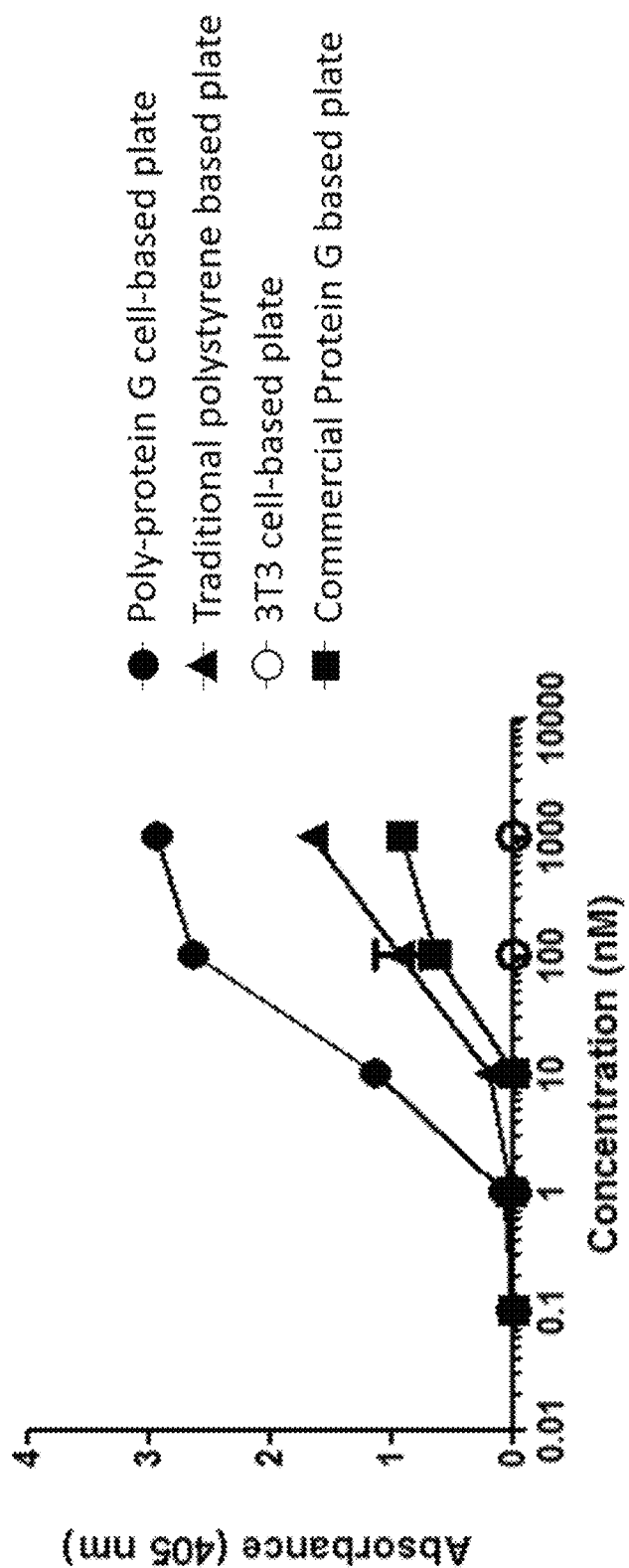
FIG. 25 shows the detection sensitivity of the PEG2K-LIPODOX by the poly-protein G cell-based plate, the traditional polystyrene-based plate and the commercial protein G-based plate in sandwich ELISA (error bar: mean=/−SD).

1 µg/mL of 15.2 Ab (an anti-PEG antibody, IgG type) was added to the poly-protein G cell-based plate, the traditional polystyrene-based plate and the commercial protein G-based plate, respectively. 0.1 nM, 1 nM, 10 nM, 100 nM and 1000 nM of PEG2K LIPODOX were added to the plates. AGP4-biotin (a biotin conjugated anti-PEG Detection antibody, IgM type), Streptavidin-HRP and ABTS were sequentially added to the plate. The resulting mixtures were measured at O.D. 405 nm. The results show that the absorbance value of the poly-protein G cell-based plate is much higher than that of the traditional polystyrene-based plate and the commercial protein G-based plate (FIG. 25).

Figure 26:
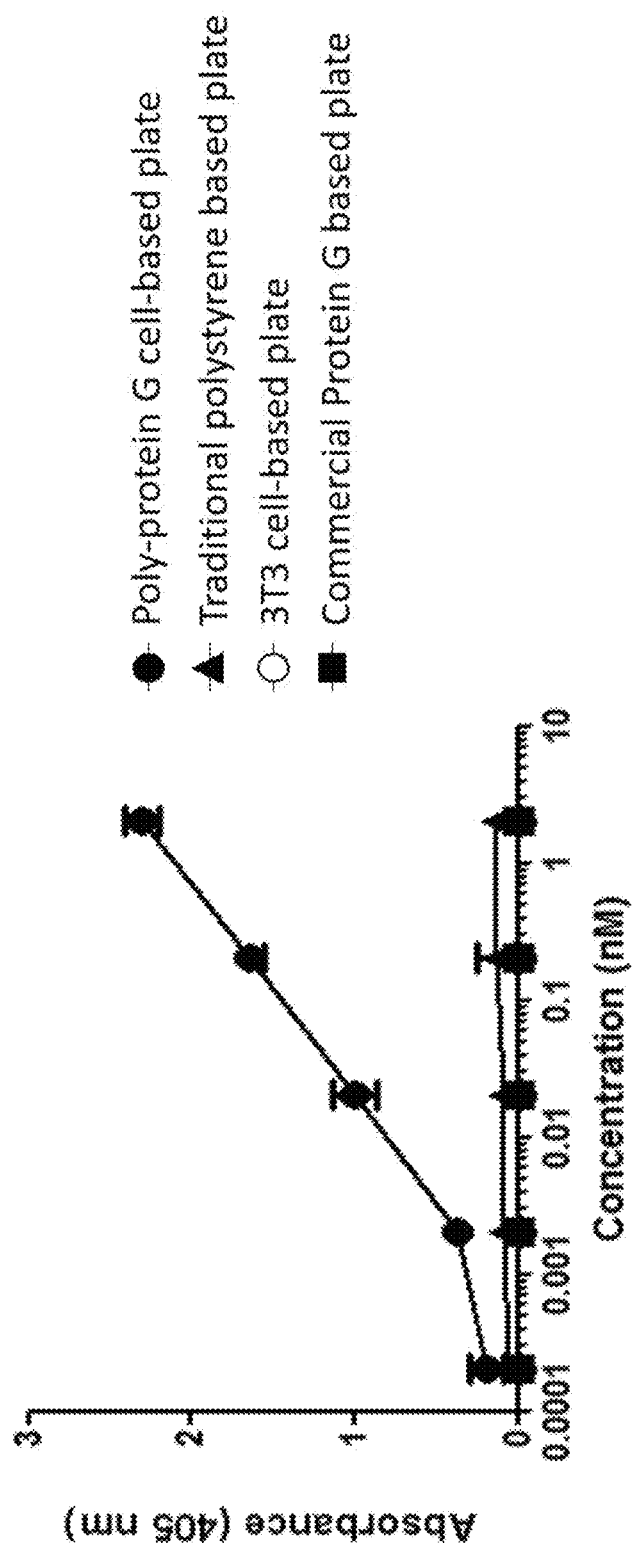
FIG. 26 shows the detection sensitivity of the PEGASYS (a PEG modified protein drug) by the poly-protein G cell-based plate, the traditional polystyrene-based plate and the commercial protein G-based plate in sandwich ELISA (error bar: mean=/−SD).

1 µg/mL of 15.2 Ab (an anti-PEG antibody, IgG type) was added to the poly-protein G cell-based plate, the traditional polystyrene-based plate and the commercial protein G-based plate, respectively. 0.00021 nM, 0.002 nM, 0.02 nM, 0.2 nM and 2 nM of PEGASYS (a PEG modified protein drug) were added to the plates. AGP4-biotin (a biotin conjugated anti-PEG Detection antibody, IgM type), Streptavidin-HRP and ABTS were sequentially added to the plate. The resulting mixtures were measured at O.D. 405 nm. The results show that the absorbance value of the poly-protein G cell-based plate is much higher than that of the commercial protein G-based plate, whereas the traditional polystyrene-based plate cannot detect PEGASYS (FIG. 26).

Figure 27:
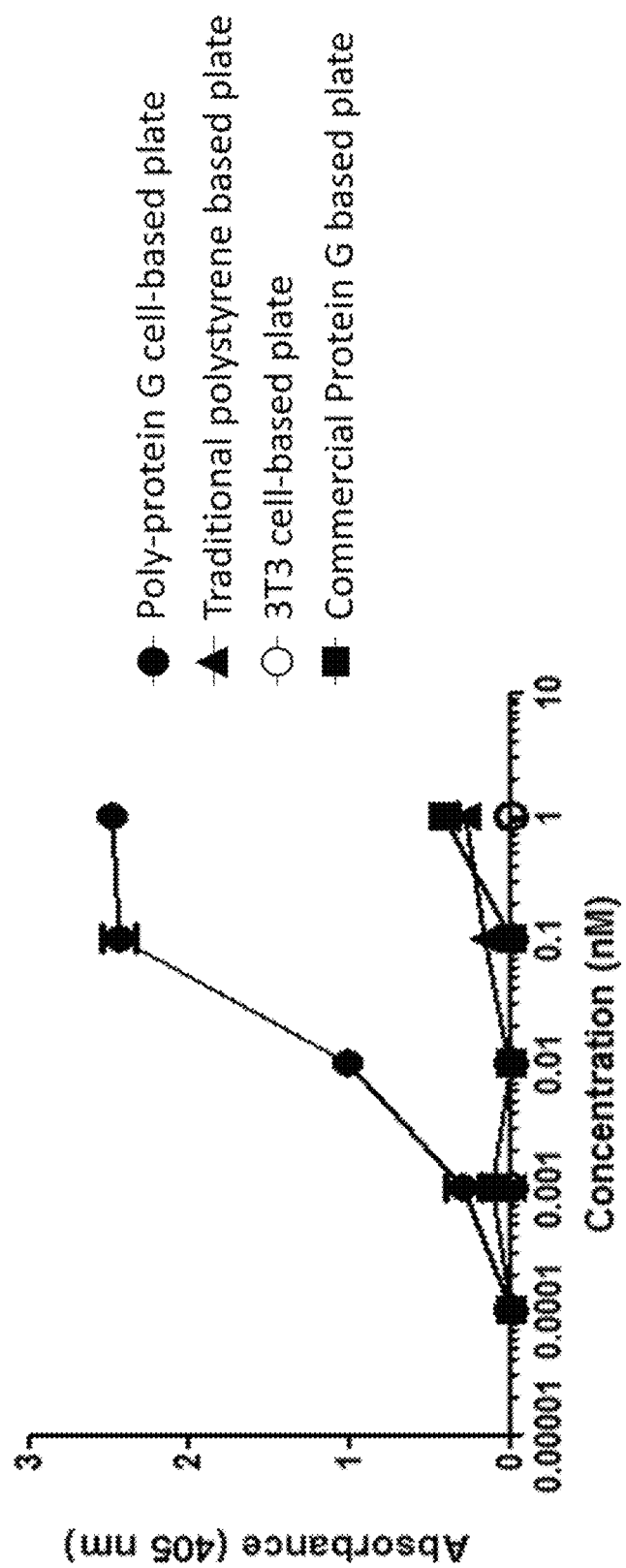
FIG. 27 shows the detection sensitivity of PEG2K-Quantum dot by the poly-protein G cell-based plate, the traditional polystyrene-based plate and the commercial protein G-based plate in sandwich ELISA (error bar: mean=/−SD).

1 µg/mL of 15.2 Ab (an anti-PEG antibody, IgG type) was added to the poly-protein G cell-based plate, the traditional polystyrene-based plate and the commercial protein G-based plate, respectively. 0.0001 nM, 0.001 nM, 0.01 nM, 0.1 nM and 1 nM of PEG2K-Quantum dot were added to the plates. AGP4-biotin (a biotin conjugated anti-PEG Detection antibody, IgM type), Streptavidin-HRP and ABTS were sequentially added to the plate. The resulting mixtures were measured at O.D. 405 nm. The results show that the absorbance value of the poly-protein G cell-based plate is much higher than that of the traditional polystyrene-based plate and the commercial protein G-based plate (FIG. 27).

Given the above, the poly-protein G cell-based plate can be effectively used in immunoassay and provides unexpected sensitivity of the immunoassay.

Figure 28:
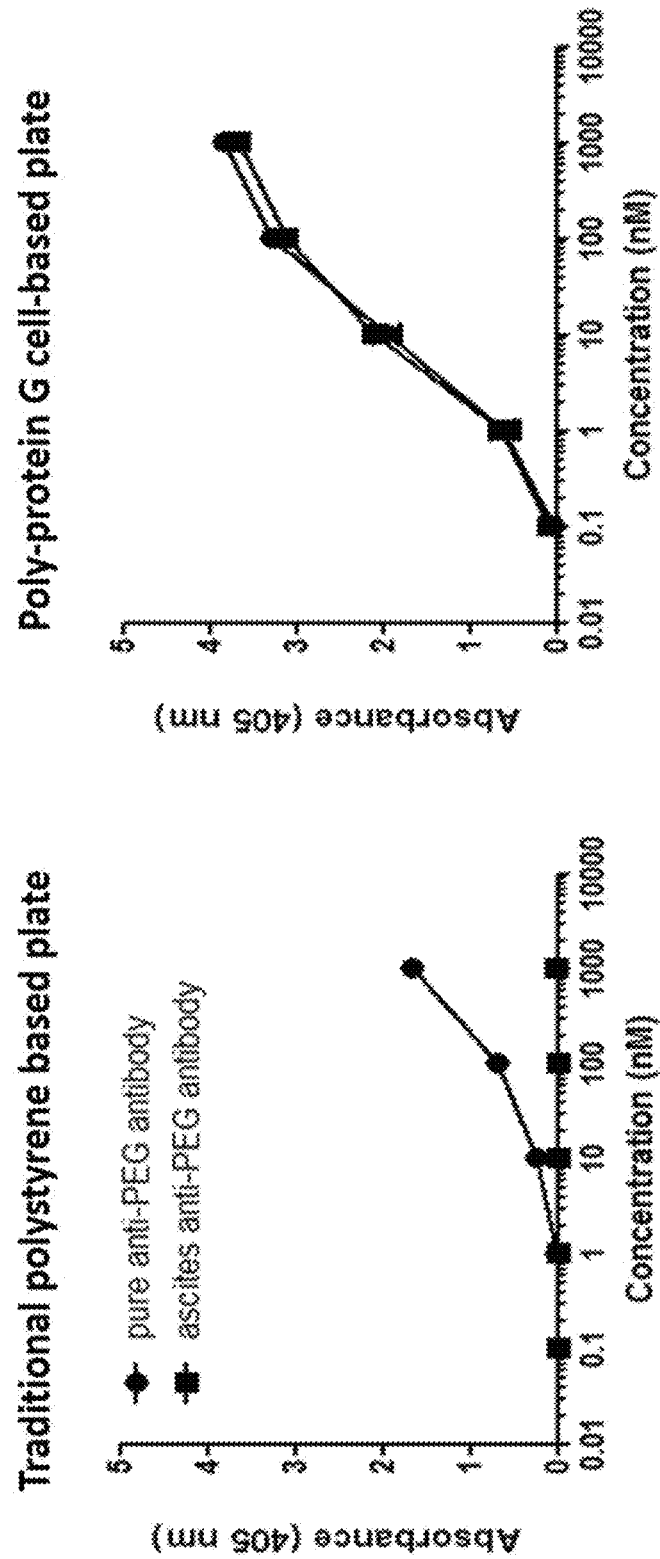
FIG. 28 shows the detection sensitivity of PEG2K-LIPODOX by the polyprotein G cell-based plate and the traditional polystyrene-based plate using the unpurified capture antibody and the purified capture antibody (error bar: mean=/−SD).
Figure 29:
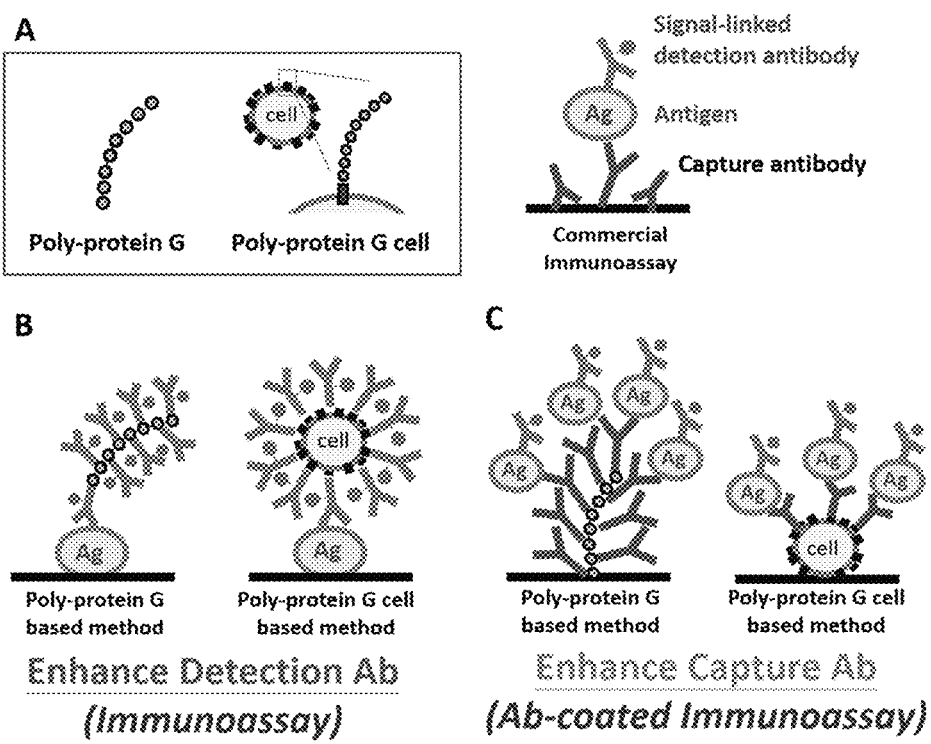
FIG. 29 A to C shows the improvement of the sensitivities and detection limits of immunoassays using various antibodies; the antibody-loading amount on the plate can significantly increase and the display of antigen binding domain (Fab) of on the plate can be unidirectional (outward).

Example 9 Unpurified Capture Antibody can be Directly Used in the Poly-Protein G Cell-Based Plate Foran Immunoassay 1 µg/mL of the purified 15.2 Ab (an anti-PEG Capture antibody, IgG type) and the ascites-15.2 Ab (unpurified) were added to the poly-protein G cell-based plate and the traditional polystyrene-based plate, respectively. 0.1 nM, 1 nM, 10 nM, 100 nM and 1000 nM of PEG2K-LIPODOX were added to the plates. AGP4-biotin (a biotin conjugated anti-PEG Detection antibody, IgM type), Streptavidin-HRP and ABTS were sequentially added to the plate. The resulting mixtures were measured at O.D. 405 nm. The results show that the traditional polystyrene-based plate can detect PEG2K-LIPODOX the when using the purified 15.2 Ab, whereas it cannot detect the PEG2K-LIPODOX when using the ascites-15.2 Ab (unpurified). However, the poly-protein G cell-based plate can effectively detect PEG2K-LIPODOX when using either the purified 15.2 Ab or the ascites-15.2 Ab (unpurified) (FIG. 28). It proves that the use of an unpurified capture antibody in the poly-protein G cell-based plate does not affect the detection sensitivity, so the protein G cell-based plate has much higher sensitivity and can reduce the antibody purification steps to save the cost.

What is claimed is:

1. A tandemly repeated protein comprising 8-20 repeats of the amino acid sequence consisting of SEQ ID NO:1 consecutively linked by a linker that links the repeats to each other to form the 8-20 repeats, wherein the linker comprises the amino acid sequence of SEQ ID NO:3.

2. The tandemly repeated protein of claim 1, wherein the tandemly repeated protein comprises the amino acid sequence consisting of SEQ ID NO:4.

3. A cell comprising the tandemly repeated protein of claim 1 expressed on the membrane of the cell, wherein the tandemly repeated protein is fused with a transmembrane protein of the cell.

4. An antibody-repeated protein complex, comprising multiple antibodies or fragments thereof bound to the tandemly repeated protein of claim 1.

5. The antibody-repeated protein complex of claim 4, wherein the multiple antibodies are detection antibodies or capture antibodies.

6. A method for detection of an analyte in a sample, comprising using the tandemly repeated protein of claim 1 to capture an analyte in a sample in an immunoassay or an antibody-coated immunoassay, and qualitatively or quantitatively detecting the analyte.

7. The method of claim 6, which comprises the steps of:
providing a solid support optionally coated with the analyte;
binding multiple detection antibodies to the tandemly repeated protein of claim 1 to form a detection antibody complex;
binding the detection antibody complex to the analyte coated in the solid support; and
qualitatively or quantitatively detecting the analyte.

8. The method of claim 6, which comprises the steps of:
providing a solid support;
immobilizing a capture antibody on the solid support;
capturing the analyte in a sample by the capture antibody;
binding multiple detection antibodies to the tandemly repeated protein of claim 1 to form a detection antibody complex;
adding the detection antibody complex to bind to the analyte; and
qualitatively or quantitatively detecting the analyte.

9. The method of claim 6, which comprises the steps of:
providing a solid support;
immobilizing the tandemly repeated protein of claim 1 on the solid support;
binding multiple capture antibodies to the tandemly repeated protein of claim 1;
capturing the analyte in a sample by the capture antibody complex;
adding a detection antibody to bind to the analyte; and
qualitatively or quantitatively detecting the analyte.

10. The method of claim 6, which comprises the steps of:
providing a solid support;
immobilizing the tandemly repeated protein of claim 1 on the solid support;
binding multiple capture antibodies to the tandemly repeated protein of claim 1 to form a capture antibody complex;
mixing a signal labeled analyte having a predetermined concentration with the analyte in a sample to form a mixture;
capturing the analyte of the mixture by the capture antibody complex; and
qualitatively or quantitatively detecting the analyte.

11. A kit for detecting an analyte in a sample, comprising a solid support optionally coated with an antigen, the analyte or a capture antibody; and the tandemly repeated protein of claim 1.

* * * * *